US006583413B1

(12) United States Patent
Shinada et al.

(10) Patent No.: US 6,583,413 B1
(45) Date of Patent: Jun. 24, 2003

(54) METHOD OF INSPECTING A CIRCUIT PATTERN AND INSPECTING INSTRUMENT

(75) Inventors: Hiroyuki Shinada, Chofu (JP); Atsuko Takafuji, Tokyo (JP); Takanori Ninomiya, Hiratsuka (JP); Yuko Sasaki, Hitachinaka (JP); Mari Nozoe, Hino (JP); Hisaya Murakoshi, Tokyo (JP); Taku Ninomiya, Hitachinaka (JP); Yuji Kasai, Hitachinaka (JP); Hiroshi Makino, Kokubunji (JP); Yutaka Kaneko, Mitaka (JP); Kenji Tanimoto, Hitachinaka (JP)

(73) Assignee: Hitachi, Ltd., Tokyo (JP)

( * ) Notice: Subject to any disclaimer, the term of this patent is extended or adjusted under 35 U.S.C. 154(b) by 118 days.

(21) Appl. No.: 09/652,606

(22) Filed: Aug. 30, 2000

(30) Foreign Application Priority Data

Sep. 1, 1999  (JP) .......................................... 11-247250
Apr. 26, 2000 (JP) ........................................ 2000-131521

(51) Int. Cl.[7] .......................... G01N 23/00; G21K 7/00
(52) U.S. Cl. ....................... 250/310; 250/311; 250/307; 250/306
(58) Field of Search ................................ 250/310, 311, 250/306, 307, 491.1, 492.2, 492.3

(56) References Cited

U.S. PATENT DOCUMENTS

| 3,813,545 | A | * | 5/1974 | Barnhart et al. ............ 250/306 |
| 4,420,686 | A | * | 12/1983 | Onoguchi et al. ........... 250/306 |
| 5,502,306 | A | | 3/1996 | Meisburger et al. |
| 5,659,174 | A | * | 8/1997 | Kaneoka et al. ............ 250/307 |
| 5,811,805 | A | * | 9/1998 | Osakabe et al. ............ 250/311 |
| 6,066,849 | A | * | 5/2000 | Masnaghetti et al. ....... 250/310 |
| 6,252,412 | B1 | * | 6/2001 | Talbot et al. .............. 324/750 |

FOREIGN PATENT DOCUMENTS

| JP | 10-27834 | 1/1998 |
| JP | 10-27835 | 1/1998 |

OTHER PUBLICATIONS

D. Hendricks et al., "Characterization of a New Automated Electron–Beam Wafer Inspection System", *Integrated Circuit Metrology, Inspection, and Process Control IX*, Feb. 20–22, 1995, Santa Clara, CA, Proceedings of SPIE, vol. 2439, May 1995, pp. 174–183.

P. Sandland et al., "An electron–beam inspection system for x–ray mask production", *Journal of Vacuum Science & Technology B*, vol. 9, No. 6, Nov./Dec. 1991, pp. 3005–3009.

D. Fleming et al., "Prospects for x–ray lithography", *Journal of Vacuum Science & Technology B*, vol. 10, No. 6, Nov./Dec. 1992, pp. 2511–2515.

* cited by examiner

*Primary Examiner*—John R. Lee
*Assistant Examiner*—Kalimah Fernandez
(74) *Attorney, Agent, or Firm*—Antonelli,Terry, Stout & Kraus, LLP

(57) ABSTRACT

A circuit pattern inspecting instrument includes an electron-optical system for irradiating an electron beam on a sample, an electron beam deflector, a detector for detecting secondary charged particles from the sample, and a mode setting unit for switching between a first mode and a second mode. An electron beam current is larger in the first mode than in the second mode, and an electron beam scanning speed is higher in the first mode than in the second mode. The circuit pattern inspecting instrument is configured so that first the sample is observed in the first mode, then a particular position on the sample is selected based on image data produced by an output of the detector in the first mode, and then the particular position on the sample is observed in the second mode.

14 Claims, 18 Drawing Sheets

COMPARISON OF INSPECTION AND REVIEW

|  | INSPECTION CONDITION | REVIEW CONDITION |
|---|---|---|
| BEAM CURRENT | >20 nA | <5 nA |
| PIXELS SIZE | >0.05 μm | <0.02 μm |
| IMAGE INTEGRATION | 1~8 TIMES | $2^n$ TIMES |
| STAGE | CONTINUOUSLY MOVING | STEP & REPEAT |
| IMAGING AREA | >50 μm | <50 μm |

SE SIGNAL OF INSPECTION MODE

SE SIGNAL OF REVIEW MODE

METHOD OF INSPECTING A CIRCUIT PATTERN AND INSPECTING INSTRUMENT

BACKGROUND OF THE INVENTION

The present invention relates to a circuit pattern inspecting instrument and a circuit pattern inspecting method, and in particular to an instrument and a method for inspecting circuit patterns on a wafer or the like in a semiconductor device manufacturing process.

For a comparison testing method of detecting defects in circuit patterns formed on a wafer in a semiconductor device manufacturing process, there has been put to practical use an instrument for inspecting the wafers by comparing images of two or more LSI circuits of the same pattern formed on a single wafer with each other.

Particularly, instruments for pattern comparison and pattern inspection using an electron beam are described in Japanese Patent Application Laid Open No. Sho 59-192943; P. Sandland et al., "An electron-beam inspection system for x-ray mask production", Journal of Vacuum Science & Technology B, Vol. 9, No. 6, November/December 1991, pp. 3005–3009; D. Fleming et al., "Prospects for x-ray lithography", Journal of Vacuum Science & Technology B, Vol. 10, No. 6, November/December 1992, pp. 2511–2515; D. Hendricks et al., "Characterzation of a New Automated Electron-Beam Wafer Inspection System, Integrated Circuit Metrology, Inspection, and Process Control IX, February 20–22, 1995, Santa Clara, CA, Proceedings of SPIE, Vol. 2439, May 1995, pp. 174–183; and Japanese Patent Application Laid Open No. Sho 5-258703. In those instruments, for obtaining a practical throughput, it is necessary to acquire images at a very high speed, and at least 100 times (at least 10 nA) the electron beam current with an ordinary scanning electron microscope is used to ensure a sufficient S/N ratio of the images acquired at high speed as well as a practical inspection speed. The electron beam diameter is spread fairly wider than that in an ordinary scanning electron microscope and is about 0.05 to 0.2 $\mu$m. This is because of an increase in chromatic aberration caused by widening of the electron energy width which is attributable to a large beam current, a limitation to brightness of an electron gun and a limitation by the Coulomb effect.

The images formed by such an electron optic system are fed to an image processing unit, in which images of the adjacent circuits of the same pattern are compared with each other for inspection. If a portion having different brightness occurs between the compared images, the portion is regarded as a defect and coordinates of the portion are stored.

With the above configuration, it is possible to detect even a defect as small as 0.1 $\mu$m or so.

Further, instruments for inspecting defects in semiconductors by reducing the energy of the electron beam with a voltage applied to a sample and an electrode disposed close to the sample are disclosed in Japanese Patent Application Laid Open Nos. Hei 7-78855, 9-181139, 10-19538, 10-27834, 10-27835, and 11-25901. But these references do not describe an instrument having a review function to be described later, or an instrument having a combination of the review function and an energy analyzing function to be described later.

SUMMARY OF THE INVENTION

Before an inspection is started using one of the above instruments, there are various parameters to be set in advance. As parameters to be set for an electron optic system there are an irradiation energy of an electron beam, a gain of a signal detection system for image forming. secondary electrons (or charged particles such as back-scattered electrons), a pixel size (a minimum picture unit), and the amount of a beam current. On the other hand, it is necessary to set a threshold value for judging whether a signal indicates a defect in comparison of two images obtained from the two adjacent areas of the same pattern by an image processing unit. If this threshold value is set too low, the defect detection sensitivity is high, but it increases a possibility that a faultless portion is judged defective. On the other hand, if the threshold value is set too high, the detection sensitivity becomes too low.

Optimum values of the above parameters differ depending on a process to be inspected, a pattern size, and a type of defects to be inspected. Therefore, it is necessary to optimize the parameters by conducting a test inspection in which an image at the coordinates of a detected defect is displayed to confirm that a defect desired to be detected has been detected, before a regular inspection.

It is also necessary to for an operator to obtain the image at the coordinates of the defect after the inspection and check what kind of defects has been detected.

In addition to acquiring an image at a high speed so as to see whether a defect is present and then detecting a defect by processing the image, it is also essential to produce an image of a specific small area and observe the image visually as in the case with an ordinary scanning electron microscope.

A mode for this observation will be hereinafter referred to as "a review mode." in this specification.

If it is necessary to make distinction between this review and the inspection mode based on high-speed acquisition of images for detecting the presence of a defect over a relatively large area, the inspection mode based on high-speed acquisition of images will be referred to as "a defect detecting inspection."

For the review, it is not necessary to form images at such a high speed as in the defect detecting inspection, but a high resolution image is needed because it is necessary, not only to recognize whether a defect is present or not, but also to recognize the shape and type of the defect to some extent.

In the conventional instruments, however, an electron optic system used therein is designed so as to be best suited for the acquisition of an image by high-speed scanning at a large current, and it has so far been impossible to obtain a resolution high enough for images for the review. Consequently, it was impossible to judge accurately whether a detected defect is a true defect or a false defect due to an erroneous detection caused by inappropriate setting of parameters. Accordingly, inspection has often been conducted with the parameters being not set to optimum values.

It is an object of the present invention to provide an inspecting instrument making possible efficient setting of the conditions for inspecting with an electron beam, defects in repeating design patterns, foreign matters, residues and the like in a semiconductor device on a wafer in a semiconductor device manufacturing process, for example.

According to the present invention, the above-mentioned object is achieved by the following configurations.

According to an aspect of the present invention, a circuit pattern inspecting instrument includes a cathode for emitting an electron beam; a stage for mounting a sample thereon; an electron-optical system for focusing the electron beam; a deflector for scanning the electron beam on the sample; a detector for detecting secondary charged particles from the sample irradiated by the electron beam; and a mode setting unit for switching between a first mode and a second mode; wherein in the first mode, a current of the electron beam is set to a first value and the electron beam is scanned at a first speed; wherein in the second mode, the current of the electron beam is set to a second value smaller than the first value and the electron beam is scanned at a second speed lower than the first speed; and wherein the circuit pattern inspecting instrument is configured so that first the sample is observed in the first mode, then a particular position on the sample is selected based on image data produced by an output of the detector in the first mode, and then the particular position on the sample is observed in the second mode.

According to another aspect of the present invention, a circuit pattern inspecting instrument includes a first electron-optical system including a first cathode for emitting a first electron beam, a first objective lens having a first focal length for focusing the first electron beam on a sample positioned at a first sample position, and a first scanning deflector for scanning the first electron beam on the sample positioned at the first sample position; a first detector for detecting secondary charged particles generated from the sample positioned at the first sample position; a second electron-optical system including a second cathode for emitting a second electron beam, a second objective lens having a second focal length shorter than the first focal length for focusing the second electron beam on a sample positioned at a second sample position, and a second scanning deflector for scanning the second electron beam on the sample positioned at the second sample position; and a second detector for detecting secondary charged particles generated from the sample positioned at the second sample position; an image-forming device for imaging the sample positioned at the first sample position based on an output of the first detector, and for imaging the sample positioned at the second sample position based on an output of the second detector; and a stage for moving a sample between the first sample position and the second sample position; wherein the first electron-optical system, the second electron-optical system, the first detector, the second detector, and the stage are housed in a single vacuum chamber; and wherein the circuit pattern inspecting instrument is configured so that first the sample is observed at the first sample position with a current of the first electron beam being set to a first value and the first electron beam being scanned at a first speed, then a particular position on the sample is selected based on image data produced by an output of the first detector, then the particular position on the sample is moved to the second sample position by moving the stage, and then the particular position on the sample is observed by enlarging the particular position on the sample using the second electron-optical system with a current of the second electron beam being set to a second value smaller than the first value and the second electron beam being scanned at a second speed slower than the first speed.

According to another aspect of the present invention, there is provided a method of inspecting a circuit pattern includes the steps of (a) detecting, using a frist detector disposed at a first position, secondary charged particles from a sample mounted on a stage and irradiated by a first electron beam scanning the sample at a first scanning speed with a current of the first electron beam being set to a first value; and (b) detecting, using a second detector disposed at a second position different from the first position, secondary charged particles from a particular position on the sample irradiated by a second electron beam scanning the sample at a second scanning speed lower than the first scanning speed with a current of the second electron beam being set to a second value lower than the first value, the particular position being selected based on an output of the first detector.

According to another aspect of the present invention, a method of inspecting a circuit pattern includes the steps of (a) providing an electron-optical system for irradiating and scanning a sample having a circuit pattern thereon by a focused electron beam, a detector for detecting back-scattered electrons or secondary electrons from an electron beam-irradiated portion of the sample, an image forming unit for forming an image of the sample based on a detected signal from the detector, and a difference detecting circuit for comparing an image signal obtained by the image forming unit with a reference image signal and thereby detecting a difference between the two image signals; (b) amplifying an output from the detector using an amplifier having a first amplification factor, the output being obtained by, scanning a relatively large region of the sample with the electron beam of a relatively large electric current at a relatively high-speed; (c) then supplying the thus-amplified output to the image forming unit to form an image signal; (d) comparing the image signal with a similar image signal obtained from another region of the sample, so as to detect a difference between the image signals; (e) determining coordinates of a position where the difference has occurred; (f) scanning a region of a smaller area than the relatively large region, including the position of occurence of the difference, with the electron beam of a smaller electric current than the relatively large electric current and at a lower speed than the relatively high speed; (g) then supplying the resulting output from the detector to the image forming unit via a circuit provided with an amplifier which amplifies the output at a larger amplification factor than the first amplification factor and is provided with a high-frequency component cut-off filter, to form an image signal; and (h) observing the difference-generating position.

BRIEF DESCRIPTION OF THE DRAWINGS

In the accompanying drawings, in which like reference numerals designate similar components throughout the figures and in which.

DETAILED DESCRIPTION OF THE PREFERRED EMBODIMENTS

Embodiment 1

Figure 1:
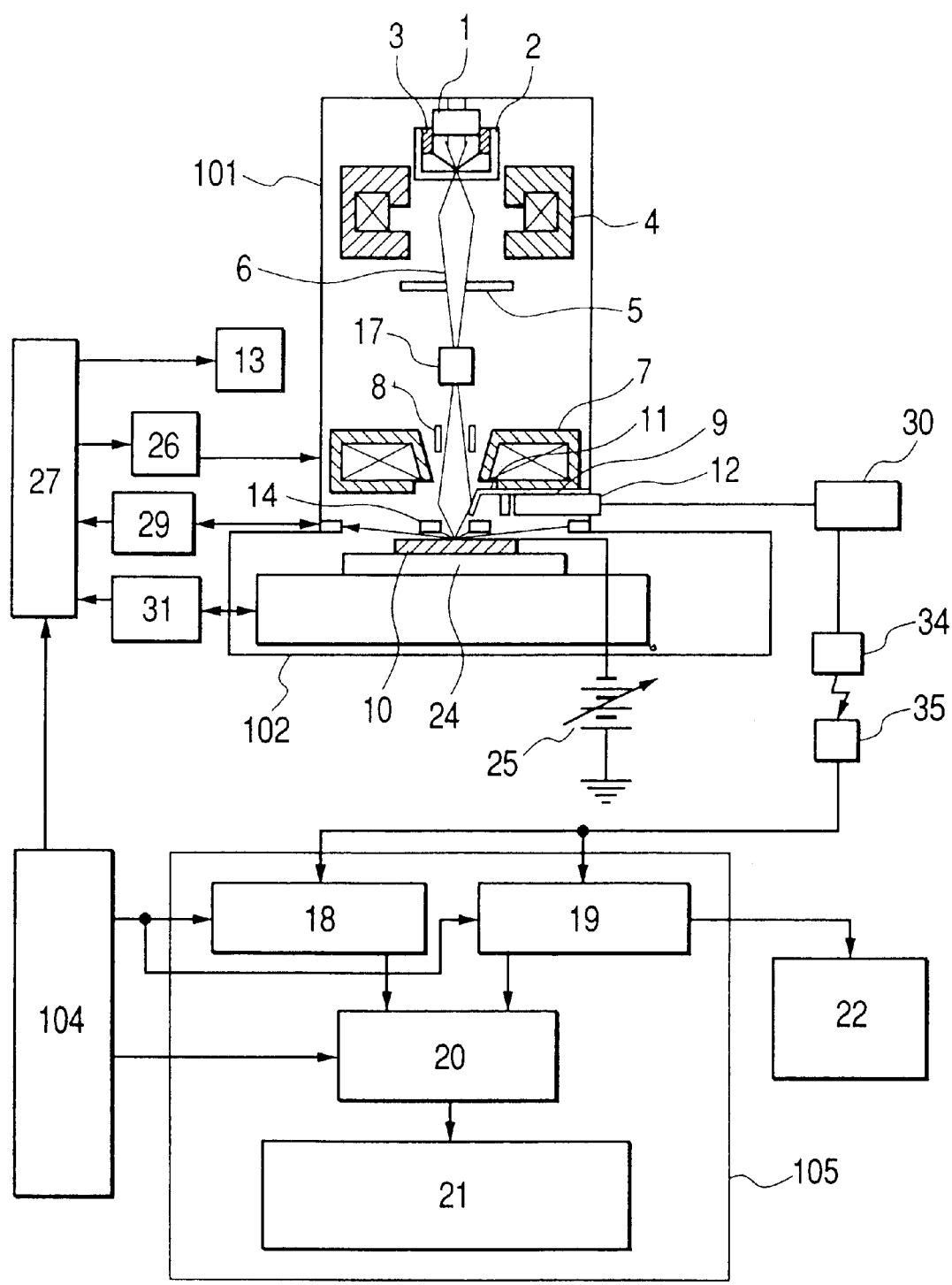
FIG. 1 is a diagram showing an example of an instrument configuration according to Embodiment 1 of the present invention.

A first embodiment of the present invention will be described below with reference to FIGS. 1 and 2, which are configuration diagrams of the present invention.

An inspection instrument of this embodiment may be divided roughly into an electron optic system 101, a sample chamber 102, a control unit 104, and an image processing unit 105.

The electron optic system 101 comprises a cathode 1, an electron beam-extraction electrode 2, a condenser lens 4, a blanking deflector 17, a scanning deflector 8, an aperture 5, and an objective lens 7.

Although in FIG. 1 a secondary electron detector 9 is disposed below the objective lens 7, it may be disposed above the objective lens 7. In this case, secondary electrons reach the detector 9 after passing through the objective lens 7. In the case where the detector 9 is located below the objective lens 71, a range of a electron beam can be made large in the objective lens, but a resolving power is limited in a "review" mode operation described subsequently because of a large aberration of the objective lens. On the other hand, where the detector 9 is disposed above the objective lens 7, the resolving power in the review mode operation can be improved because the aberration of the objective lens can be made smaller, but the deflection range becomes small. Thus, both the two arrangements of the secondary electron detector have merits and demerits. One of the configurations may be selected depending upon application of the inspection instrument. A positive high voltage is applied to the detector 9. A ground level of a preamplifier 12 and that of a detection circuit 30 both connected to the detector 9 rides on the positive high potential applied to the detector.

An output signal from the secondary electron detector 9 is amplified by the preamplifier 12 and is converted into a digital data signal by the detection circuit 30. This signal is converted into an optical signal by an optical transmitter 34.

The optical signal is then received by an optical receiver 35 which is at the ground potential level, is converted into an electrical signal, and then is fed to the image processing unit 105.

Figure 2:
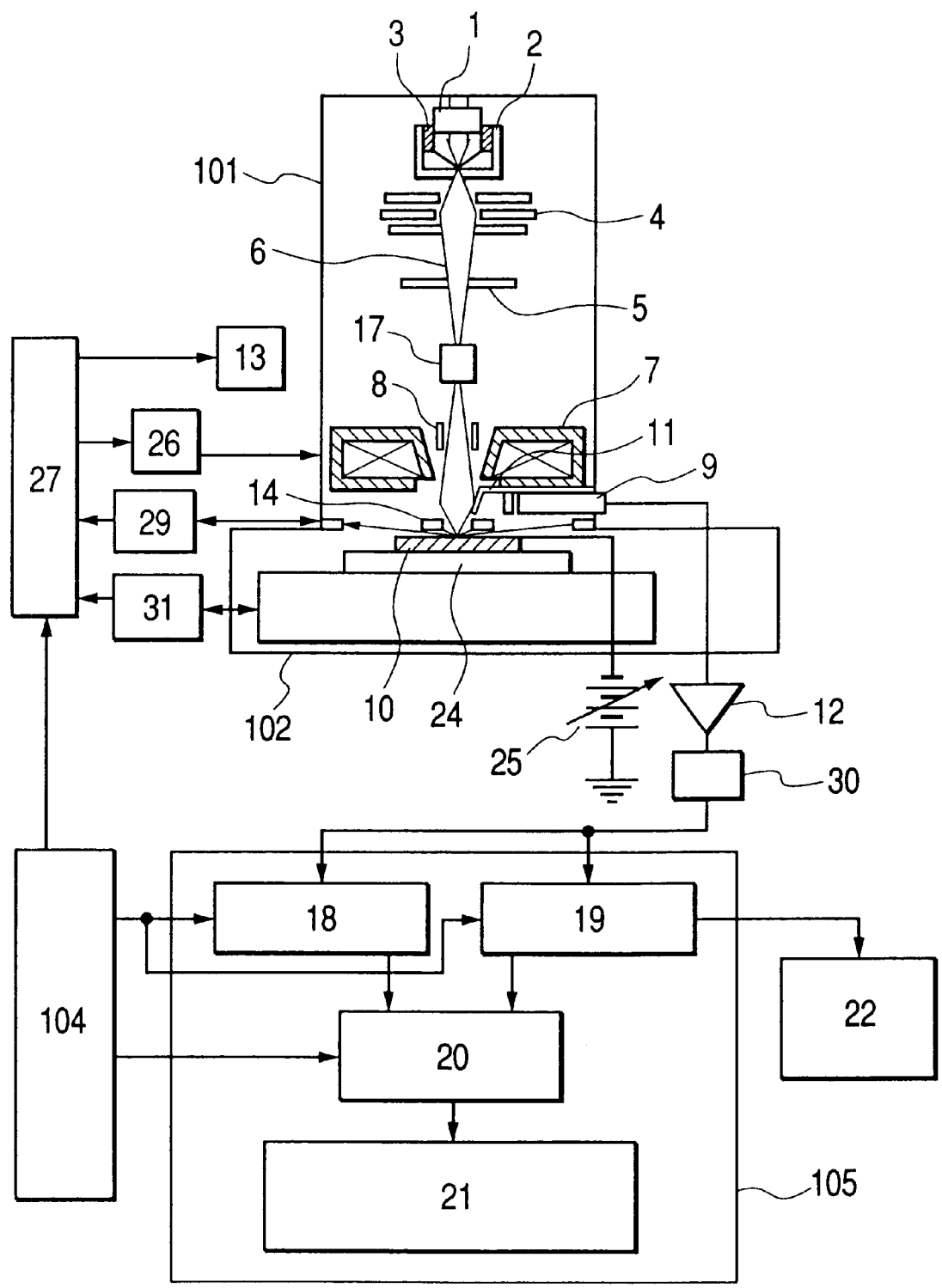
FIG. 2 is a diagram showing a modification of the instrument configuration of Embodiment 1.

Although in FIG. 1 the condenser lens 4 is formed by an electromagnetic lens, it may be formed by an electrostatic lens as shown in FIG. 2. For example, a so-called einzel lens is most suitable for the electrostatic lens. The einzel lens is comprised of three plate electrodes arranged axially and two outside ones of the three plate electrodes are at the ground potential and a central one of the three is supplied with a positive or negative voltage. But an electrostatic lenses other than the einzel lens can be used. An electrostatic lens makes possible reduction of the size of the electron optic system.

Returning to FIG. 1, the sample chamber 102 is comprised of a stage 24, an optical height sensor 29, and a stage position measuring unit 31 which uses a laser length measuring unit or a linear scale.

The image processing unit 105 is composed of image memory units 18 and 19, a calculation unit 20, and a defect recognizing unit 21. An electron beam image which has been received is displayed on a monitor 22. Instructions and conditions for operations of various components of the inspection instrument are inputted into and outputted from the control unit 104. Conditions such as an acceleration voltage for electron beam generation, a deflection width of the electron beam, a deflection speed, a moving speed of a sample stage, and detector signal pick-up timing are inputted beforehand to the control unit 104. Further, a correction signal is generated based upon signals from the optical height sensor 29 and the stage position measuring unit 31 and is fed to an object lens power supply 26 and a scanning signal generator 13.

Figure 3:
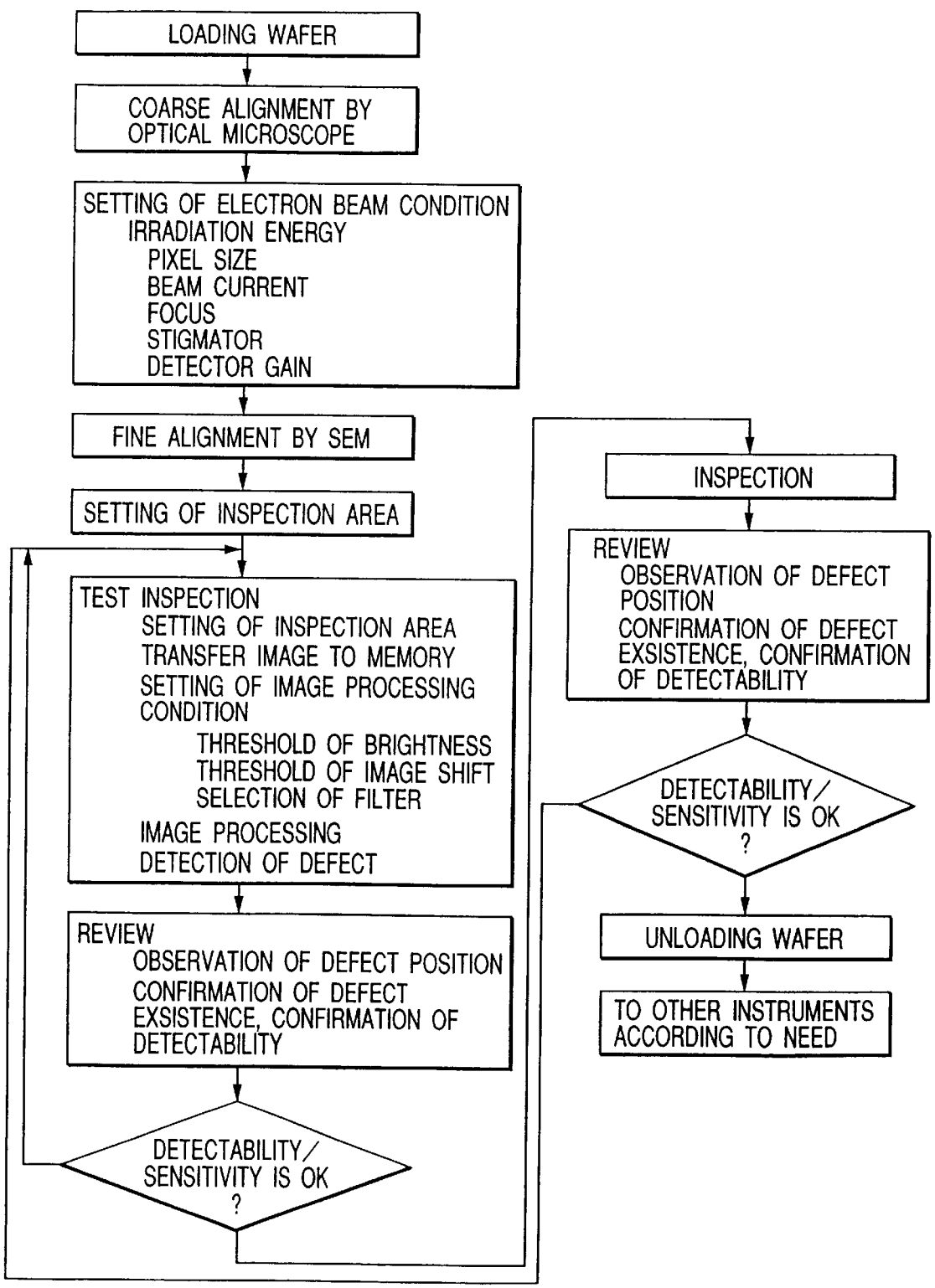
FIG. 3 is a diagram showing an example of an inspection flow in the present invention.

FIG. 3 is a diagram showing a flow of inspection of an external appearance of a pattern in a semiconductor device using an electron beam. With reference to FIG. 3, the following explains a flow of inspection of an external appearance of a pattern in a semiconductor wafer according to the present invention.

After loading of a wafer, a coarse alignment of the wafer is performed using an optical microscope. The reason is that an area scanned by an electron beam in a subsequent operation is so small that there is a possibility that an alignment mark on the wafer positioned mechanically in the loading operation is outside the small scanned area. Therefore, the alignment of the wafer by using an optical microscope providing a wide viewing field and a low magnification image is performed with an accuracy of about several tens $\mu$m.

Next, conditions for the electron optic system are established. Electron beam irradiation energy, a pixel size (a minimum image unit), and a beam current are set in accordance with the type of a pattern on a wafer to be inspected. An optimum electron beam irradiation energy differs depending on a material forming patterns.

Usually, in the case of an electrically conductive material, a rather high energy of several keV or more is used for attaining high resolution, while in the case of a pattern containing an insulating material, the energy level is set at 1.5 keV or less for antistatic purposes.

Next, a pixel size is determined in view of a defect size to be specially noted. If the pixel size is set excessively small, a time required for inspection will increase excessively. Next, an electron beam current is set. There is a default value of an electron beam current specific to each electron-optical system. But, in the case of a wafer which is easily charged electrically, it is preferable that the beam current is set low, and if the contrast of a defect to be detected is known to be large beforehand, a high-sensitivity inspection can be performed by focusing a smaller beam current into a narrower electron beam.

Then, an electron beam image of the wafer to be inspected is displayed and correction is made for a focal point and astigmatism. This can be done automatically by picking up the image and executing the correction on a computer or with use of a dedicated image processing unit.

After completion of the above setting, a fine alignment of the electron beam image is executed, whereby a coordinate system of the stage and that of the wafer become coincident with each other exactly. By measuring the coordinates of the stage with a laser length measuring unit for example it becomes possible to inspect a desired position on the wafer.

Next, an area to be inspected is inputted from a control display, such as a display of a work station for control.

Then, a test inspection is conducted for judging whether the various parameters established above are appropriate or not. First, part of a pattern to be inspected is designated. This is an area designation in the test inspection. The test inspection is then carried out. In the test inspection, images are detected using an electron beam in the same manner as in the regular defect detecting inspection, and all the acquired images are stored in memory without passing through an image processing circuit.

Next, image processing conditions are established, which conditions are thresholds for judging whether a defect is present or not when two images from two adjacent patterns of the same design are compared with each other in the image processing unit. If the thresholds are set too low, the defect detecting sensitivity is improved, but it increases a possibility that a faultless portion is judged defective. On the other hand, if the thresholds are set too high, the detection sensitivity becomes too low.

In FIG. 3, a threshold of brightness indicates a threshold of a difference between brightness signals of two images. Electron beam images are very rough (i.e., a low S/N ratio of the image) compared with optical microscope images. Therefore, even in a case in which two identical objects are compared and two images obtained from the two identical objects have the same average brightness, a difference in brightness is present when two corresponding pixels of the two images are compared. In view of this, a threshold of a brightness difference is established, and only a portion producing a brightness difference above the threshold value is detected as a defect when two images from two patterns of the same design are compared, so that a brightness difference between two images caused by roughness produced in the two images may not be judged as a defect.

A threshold of an image shift is established so that an error in alignment of two images to be compared may not be judged as a defect. Assuming an image shift below the above-established threshold of an image shift may occur, and only a portion indicating an image shift above the threshold of an image shift is judged as a defect.

As to a selection of a filter indicated in FIG. 3, filtering is applied to an obtained image so as to reduce roughness or enhance edges of the detected image. An optimum filter is selected by trial and error depending upon the type of a pattern and defects to be detected.

After the above parameters have been established, image processing is executed. The image processing in the test inspection performs a comparison inspection using a series of already acquired images. The comparison inspection detects a defect and stores coordinates of the defect, then displays the position of the defect on the control display. If no defects are detected at this time point, the already established thresholds of the image processing parameters are lowered to enhance the detection sensitivity and the comparison inspection is conducted again with use of two-dimensional information in a memory.

Next, an image at the coordinates of the defect detected in the test inspection is observed. This is the "review". Since the image of the portion concerned has already been stored in memory, first the image is displayed on a display of the control work station or on a display dedicated to an image display and a visual observation is made to see what kind of defect has been detected. As to a fairly large defect, the shape and type of the defect become clear easily by visual observation. However, if a fine defect is of the size close to a limit size capable of being detected by the inspection instrument or is of a small contrast, it is often difficult to judge the defect sufficiently clearly with visual observation. Then, the conditions of the electron optic system are changed over to the conditions of the review so that a high resolution image is produced and it can be easily decided whether the defect detected in the test inspection is a true defect or a defect intended to be detected. Based upon this result, the image processing parameters are modified and the review is performed again to find out conditions to ensure detection of a defect intended to be detected.

The conventional instrument is not provided with the high-resolution review conditions and is designed to form images with a large-current electron beam, and therefore, if observation is continued over a long period of time and a sample is irradiated with a large quantity of electrons, damaging or charging of the sample may occur and make it impossible to observe the sample. The conventional instrument is intended only for detection of defects and has not a sufficient resolving power for visually judging the details of defects. Consequently, trial and error must be repeated in the review and in the setting of the image processing parameters, thus requiring a large amount of time.

According to the present invention, however, because of a good quality of the review display, it is possible to accurately judge whether the selected image processing parameters are proper or not, and the number of times of trial and error has decreased remarkably. As a result, the time of manned operation of the instrument was greatly shortened and an overall operating efficiency of the instrument was improved.

When the review for setting of the conditions is completed, the defect detecting inspection is started and an unmanned operation is carried out automatically. Another review is conducted again upon completion of the defect detecting inspection. After it has been confirmed by the review whether the detected defect is a true defect or not, the wafer is unloaded. If necessary, the wafer is then transferred to other analyzing and inspecting instruments for various analyses and inspections.

Figure 4:
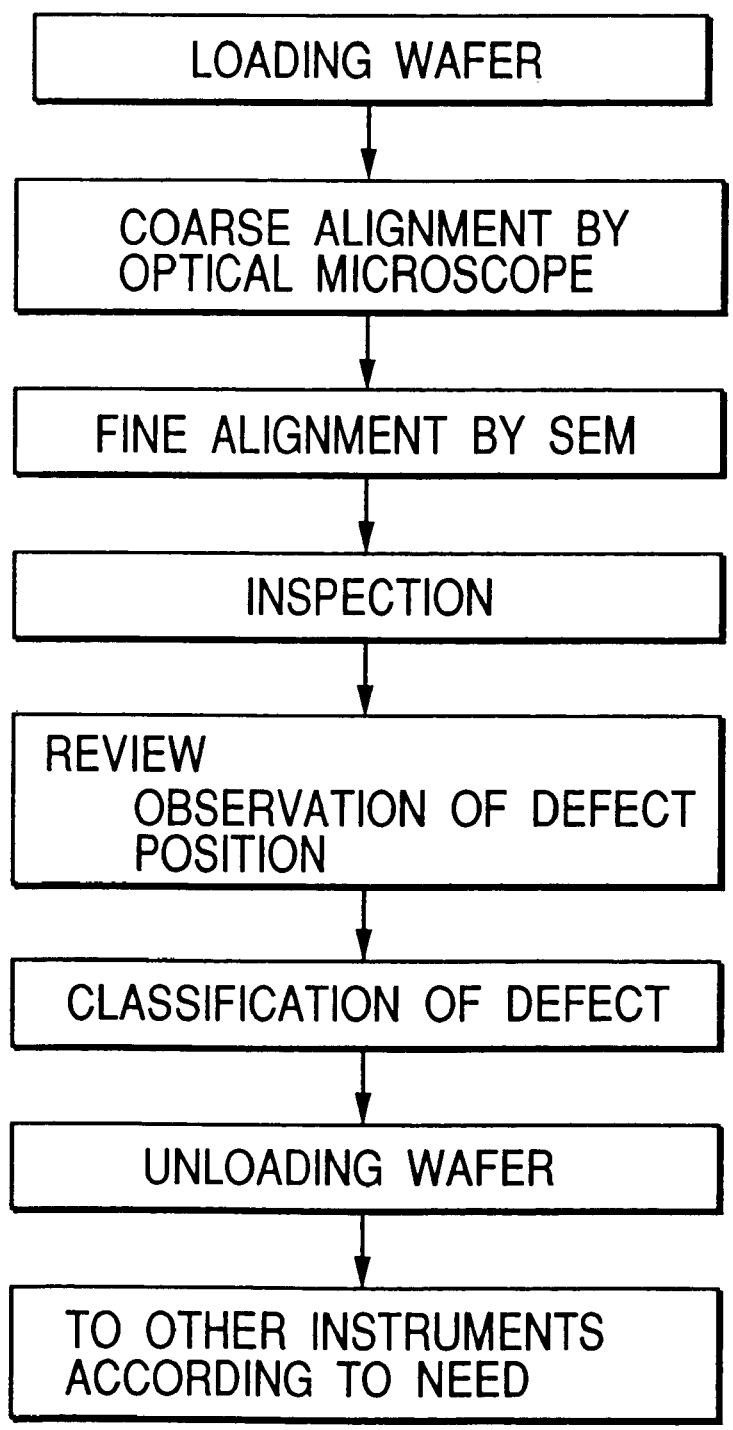
FIG. 4 is a diagram showing another example of an inspection flow in the present invention.

In the case of an automatic inspection of a wafer for which conditions of defect detecting inspection have already been established, the defect detecting inspection mode and the review mode are performed according to a flow shown in FIG. 4. More specifically, just after loading of the wafer, the defect detecting inspection is carried out under the existing conditions which have been set, and the review mode is conducted after the defect detecting inspection. In the review mode, the detected defects are classified depending upon kinds of defects such as foreign matters, electrical defects, and defective shapes.

The following describes the specifications and features of the conditions of the review and the defect detecting inspection and the differences between the conditions of the review and the defect detecting inspection, which are the main points of the present invention.

Figures 5, 6:
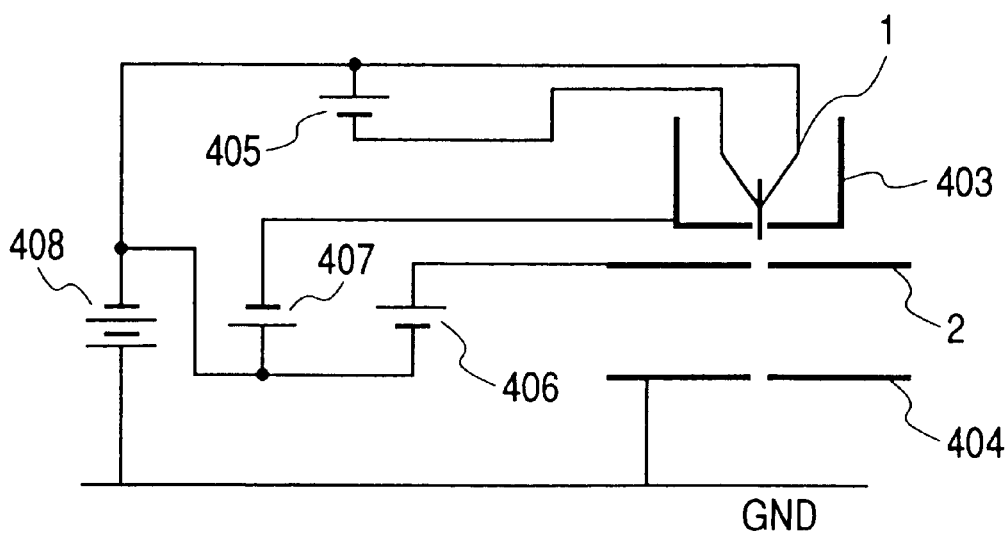
FIG. 5 is a diagram showing conditions for an inspection and a review.
FIG. 6 is a diagram explaining part of Embodiment 1.

FIG. 5 shows a comparison in performance between the conditions of the defect detecting inspection and the review with respect to performance.

The conditions of the defect detecting inspection permit a very high-speed acquisition of images for inspecting the entire wafer surface in a practical period of time. The time required for forming an image corresponding to 100 μm square image with a pixel size of 0.1 μm is at most 20 msec. For a high-speed acquisition of images, the stage is moved continuously and the electron beam is scanned in a direction nearly perpendicular to the movement of the stage. Further, the instrument is designed so as to provide a beam current of at least 20 nA for realizing a high-speed image formation with an S/N ratio sufficient for the inspection. More specifically, the current density obtainable from the cathode was set at least 0.2 mA/sr. A large lens aperture compared with that of a high-resolution SEM was used and a taking-angle α of an electron beam from the cathode (i.e., a beam divergence half-angle of a portion of the electron beam emitted from the cathode at a wide angle which irradiates the sample) was set at least 6 mrad. The pixel size serving as the minimum image unit was set equal to the minimum defect size desired to be detected. At present, the minimum size of defects which pose a problem is approximately 0.05 μm and therefore the pixel size was set at least 0.05 μm. This value means that the pixel size can be set larger than 0.05 μm because a larger defect size than 0.05 μm may be found in some wafers. In some manufacturing processes of wafers to be inspected, there sometimes is a case where the quantity of secondary electrons generated is small and a sufficient brightness is not obtained by a single scanning of an electron beam. In such a case, images obtained by scanning an electron beam on the sample in a plural number of times may be added together. But the smaller the number of times of the scanning, the better, because of the problem that the inspection time becomes longer. As to the imaging area, or the field of view, the larger, the better, and therefore it was set at least 50 μm, with 100 μm being a standard.

On the other hand, in the review conditions, the current value need not be large and a current value of 5 nA at most suffices because the image forming speed is not required to be so high. As to the pixel size, it is required to be equal to or less than one-fifth of the defect size for observing the shape of each defect in detail. Therefore, the pixel size was set equal to or less than 0.02 μm. As to the addition of images, it was set at 2 the nth power, with no upper limit. In the review, for observing a specific site carefully, the stage is stopped and the electron beam is scanned in two dimensions. Further, for observing a magnified defect, it is necessary that the imaging area be small, which is at most 50 μm.

Thus, there is a great difference in considering the pixel size between the inspection and the review mode. In the inspection, even if a probe size is larger than the defect size, it suffices to judge whether a defect is present or not. That is, it suffices for the probe size and pixel size to be equal to or larger than the defect size. If the pixel size is small, the quantity of electrons irradiated per unit area becomes smaller and the clock becomes slow due to a long-time radiation, thus giving rise to a problem that the high-speed inspection is not possible. On the other hand, in the review mode, a sufficient time is taken for acquiring the image of a defect and a probe size of equal to or less than one-fifth of the defect size is required. In the present invention, not only the probe size is changed, but also the pixel size is changed accordingly between inspection and review.

Now, a more detailed description will be given below about how conditions are changed over between the defect detecting inspection and the review.

First, the components of the electron optic system and the operation thereof will be described in detail with reference to FIG. 1.

As the cathode 1, a field emission type cathode, particularly a diffusion-supply type thermionic field-emission (Schottky emission) cathode, is preferable, and this electron optic system employed a so-called Zr/O/W type cathode comprising a tungsten tip provided with a coating layer made of zirconium and oxygen thereon. This cathode provides stable electron emission over a long time. Further, an angular electron intensity can be set freely in the range of 0.001 to 1 mA/sr by varying the extraction voltage. However, with increasing current density, the energy width of emitted electrons also increases, thus leading to an increase of chromatic aberration. An electron beam current of at least 20 nA was necessary for the inspection, and therefore the angular intensity of electron beams emitted from the cathode 1 is set in the range of 0.2 to 1 mA/Sr.

The electron beam 6 is extracted from the cathode 1 by applying an appropriate voltage to the extraction electrode 2. The electron beam 6 is accelerated by a high negative voltage applied to the cathode 1. The acceleration voltage could be set at 10 kV or more. This is for suppressing the aforesaid chromatic aberration caused by an increase in energy width of the electron beam ascribable to the use of a large-current electron beam and also for suppressing a phenomenon (the Coulomb effect) in which a large-current electron beam becomes too wide due to mutual repulsion of electrons to be narrowed.

The electron beam 6 travels toward the stage 24 with an energy of about 10 kV, then is focused by the condenser lens 4 and is further focused into a narrow beam by the objective lens 7, then is irradiated onto a substrate 10 (a wafer, a chip or the like) to be inspected on the stage 24.

The scanned area was set at 50 μm square or more and a distance (an operational distance) between the objective lens 7 and the substrate 10 to be inspected was set at 25 mm in order to ensure a distortion-free image even at a peripheral portion. As a result, a focal length of the objective lens 7 became as long as about 30 mm.

The substrate 10 to be inspected is provided with negative-voltage applying means for the application of a negative voltage from a high voltage power supply 25. By adjusting the high voltage power supply 25 it becomes easy to adjust the irradiation energy of the electron beam irradiating the substrate 10 at an optimum value. Given that this voltage is 9.5 kV and the acceleration voltage. of the electron beam is 10 kV, the energy irradiated onto the sample is 500 eV.

An image is obtained by a method in which the electron beam 6 is scanned in only one direction and the stage 24 is moved continuously in a direction perpendicular to the scanning direction.

The detection of signals for image formation is conducted in the following manner. Secondary electrons are generated by the electron beam 6 irradiated to the sample 10. Since the secondary electrons is accelerated rapidly by the voltage applied to the sample 10, it is difficult to draw in the secondary electrons directly to the detector 9. Therefore, between the substrate 10 and the detector 9 are disposed a deflector formed by a combination of an electric field and a magnetic field, e.g., an ExB deflector 14, and a converter electrode 11 for converting the accelerated secondary electrons into slow secondary electrons.

The ExB deflector 14 is a deflector wherein an electric field and a magnetic field are orthogonal to each other, for the primary electron beam 6 which enters the ExB deflector 14 from above, a deflecting action induced by the magnetic field and a deflecting action-induced by the electric field are opposite in direction and cancel each other, while for the secondary electron beam which enters the ExB deflector 14 from below, both such deflecting actions are added together.

After being deflected by the ExB deflector 14, the secondary electrons are irradiated onto the converter electrode 11 and secondary electrons generated from the converter electrode are detected by the detector 9. As the detector 9 was used a PIN type semiconductor detector for realizing a large current (at least 10 nA) high-speed detection. The secondary electron signal thus detected is amplified by the preamplifier 12, then the amplified signal is subjected to A/D conversion in the detection circuit 30, and the resulting digital signal is fed to the image memory unit 18 or 19 which stores data obtained from the secondary electron signal and corresponding to a two-dimensional image of the sample. Next, the substrate 10 to be inspected is moved by movement of the stage 24, the substrate 10 is irradiated with the electron beam 6 emitted from a field emission cathode serving as the cathode 1, and then a secondary electron signal obtained are used to perform a comparison inspection.

In this way, images of two adjacent semiconductor patterns of the, same design spaced several $\mu$m from each bother are compared and judged at a high speed in the calculation unit 20 or the defect recognizing unit 21, and thereby a defect is detected. The detection of a defect can also be effected by comparing images of two patterns of the same design on two different chips.

The following describes how to change over to the review mode.

The following are main factors of limiting resolution in the defect detecting inspection mode: 1) chromatic aberration caused by variations in energy of electrons in focusing by a lens, 2) the Coulomb effect caused by mutual repulsion of electrons due to a high current density, 3) a finite diameter of an electron source due to the fact that a tip end of the cathode is not a point source. The basics in the change-over to the review mode is such that the electron beam current is made smaller than that in the defect detecting inspection, thereby suppressing obstacles to focusing the electron beam into a fine beam, such as aberration of the optical system and the Coulomb effect, and thereby forming a high-resolution image with a fine electron beam. Concrete methods will be enumerated below.

A first method is lowering the current density extracted from the cathode. FIG. 6 illustrates a configuration of an electron gun. In FIG. 6, a cathode 1 is a so-called Zr/O/W type Schottky emission cathode comprising a tungsten tip provided with a coating layer thereon made of zirconium and oxygen. A filament in the cathode 1 is heated by passing an electric current therethrough from a heating power supply 405. A tip end of the cathode projects from a central hole in a suppressor electrode 403 for suppressing unwanted thermoelectrons.

A potential negative with respect to the cathode 1 is applied to the suppressor electrode 403 from a Vs power supply 407. The tip end of the cathode 1 is opposed to an extraction electrode 2 and a potential positive with respect to the cathode 1 is applied to the extraction electrode 2 from an extraction power supply 406. The power supplies 405, 406 and 407 are floating negative by an amount corresponding to a desired acceleration voltage by means of an acceleration power supply 408. As a result, the electron beam extracted from the cathode 1 is accelerated during its travel to an anode 404 at ground potential. In the electron gun thus constructed, the current density extracted can be reduced by reducing an extraction field at the tip end of the cathode. This can be attained by increasing the voltage value of the power supply 407 connected to the suppressor electrode 403 or lowering the potential of the extraction electrode 2.

Figure 7:
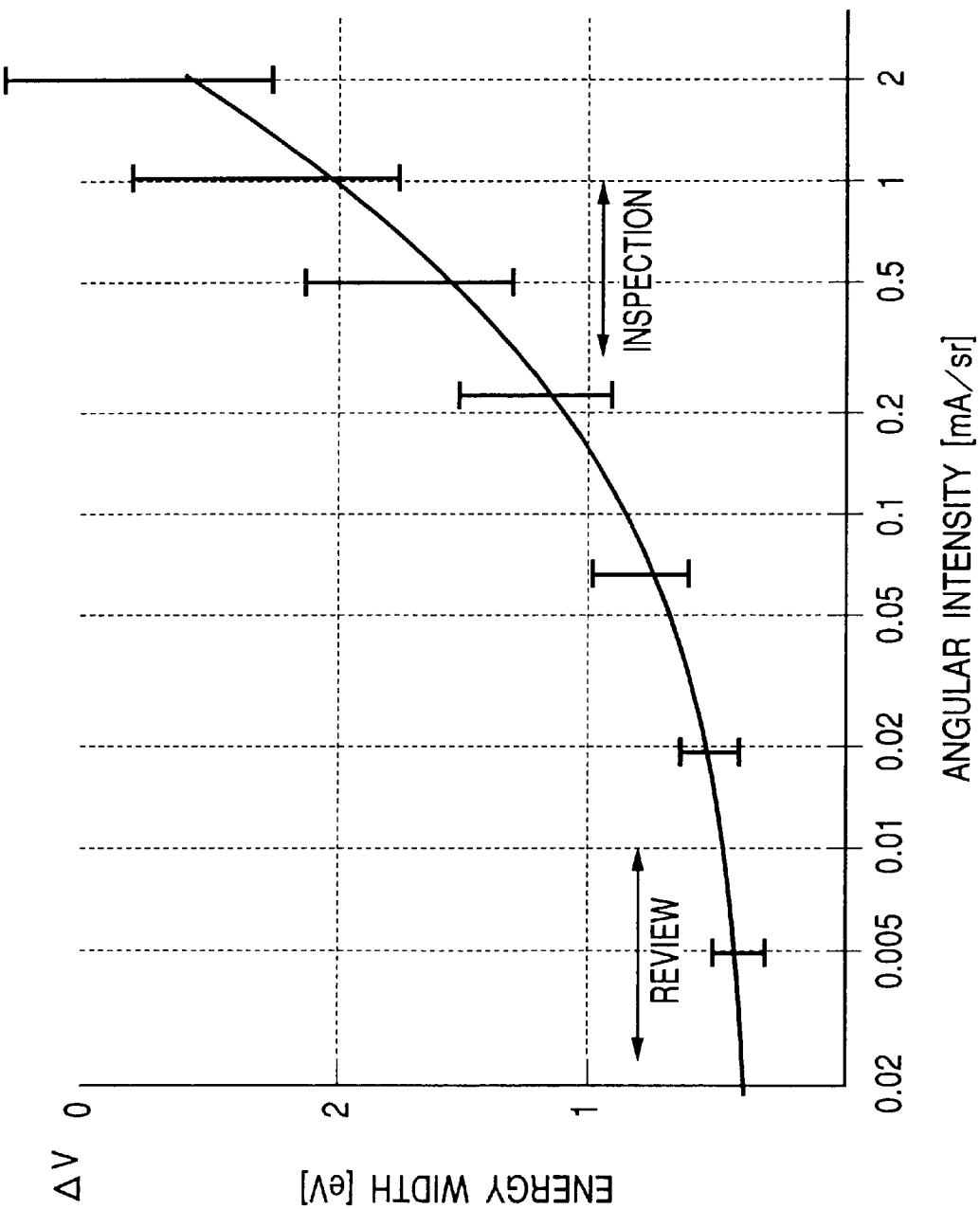
FIG. 7 is a diagram illustrating an operating principle of Embodiment 1.

The following explains the reason why aberration can be reduced by reducing the current density. FIG. 7 shows an angular current intensity of electrons emitted from the cathode and a half-width (hereinafter an energy width) of energy variations of electrons in the emitted electron beam. The energy variations in electrons cause chromatic aberration of a lens in the electron optic system. Chromatic aberration is proportional to the energy width as expressed in Equation 1. Thus, if the energy width is halved, chromatic aberration also is halved. The angular current density for the defect detecting inspection is in a range of from 0.1 mA/sr to 1 mA/sr, and that in the review mode is in a range of from 0.001 mA/sr to 0.01 mA/sr. With these conditions, the beam current becomes about 100 nA in the defect detecting inspection and about 5 nA or less in the review mode, and it is seen from FIG. 7 that the energy width becomes one-third and that chromatic aberration also becomes one-third. As a result, the beam diameter also becomes one-third or so and thus the resolution is improved.

$$dc = Cc \cdot \Delta V \cdot \alpha / V_0 \qquad (1)$$

dc: beam diameter caused by chromatic aberration
$\Delta V$: energy width
Cc: chromatic aberration coefficient
$V_0$: acceleration voltage
$\alpha$: beam-divergence half-angle A second method of improving resolution by reducing an electrical current is replacing the aperture (e.g., the aperture 5 in FIG. 1) with an aperture of a smaller diameter to reduce aberration. As expressed in Equation 1, chromatic aberration of the optical system is proportional to the beam divergence half-angle $\alpha$. Therefore, if the diameter of the aperture which determines the beam divergence half-angle is halved, chromatic aberration also is halved. If the beam divergence half-angle is set too small, diffractive aberration in inverse proportion to the beam divergence half-angle increases. But if the beam divergence half-angle is about 1 mrad or more, the diffractive aberration poses no problem and therefore the beam diameter also becomes nearly half. However, this method requires the use of a mechanical aperture moving mechanism and thus involves problems with reliability and ease of use.

Figure 8:
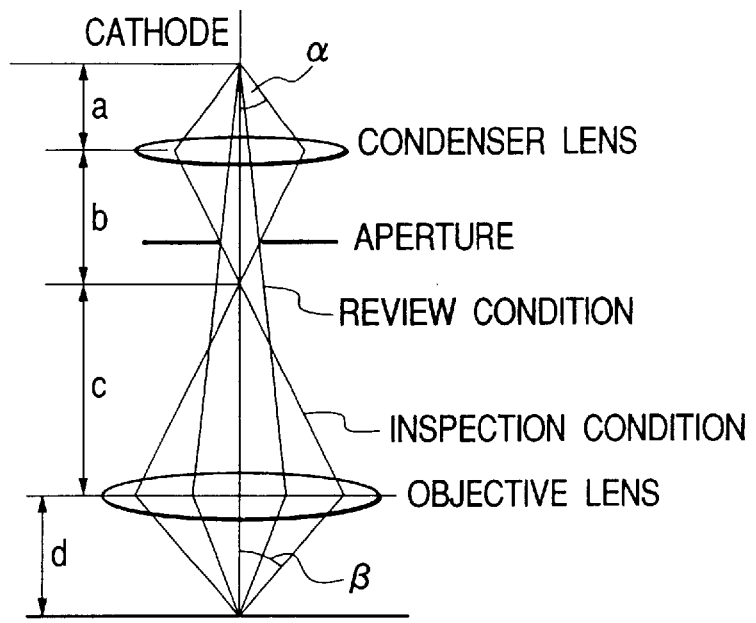
FIG. 8 is a diagram also illustrating the operating principle of Embodiment 1.

A third method is changing the focal length of a lens so as to change the magnification of the optical system and thereby reducing the beam divergence half-angle without moving the aperture. This method is superior to the second method because the size of the electron source in the cathode can also be reduced. This will now be described with reference to FIG. 8.

In the defect detecting inspection, an electron beam emitted from a cathode is focused to form an image (which is called a crossover) by a condenser lens and then is again focused onto a sample by an objective lens On the other hand, in the review mode, the beam taking in half-angle $\beta$ from the cathode is reduced by making the lens action of the condenser lens zero and a beam half-angle $\beta$ of irradiation by the objective lens also becomes narrow.

As a result, the current value is reduced and the chromatic aberration of the objective lens is reduced to improve resolution. Moreover, the magnification of the entire optical system, which was (b/a)×(d/c) in the defect detecting inspection, becomes as small as d/(a+b+c) in the review mode, so that the electron source in the cathode can be reduced in size and hence the resolution is further improved. An electromagnetic lens is used as the condenser lens and it is composed of a coil and a magnetic path. The strength of the lens action can be controlled by adjusting the value of an electric current flowing through the coil, so when the lens action is desired to be made zero, the current value may be made zero. Although the description has been directed to the case where the action of the condenser lens is made zero, even if the lens action is not made completely zero, the same advantage as above can be expected by adopting such a weak lens condition that a crossover is not formed.

Figure 9:
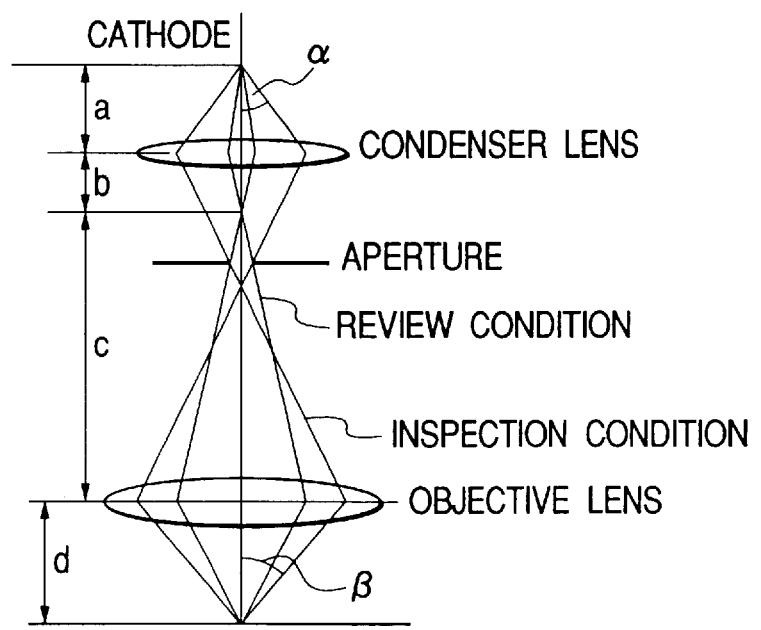
FIG. 9 is a diagram showing an example of the operation principle of Embodiment 1.

Also by increasing the strength of the condenser lens in comparison with that in the defect detecting inspection and thereby shifting the position of a crossover to a position above the aperture, it is possible to improve the resolution. This is illustrated in FIG. 9. The effect obtained is the same as in the case of making the lens action of the condenser lens zero. That is, the magnification of the optical system is expressed by (b/a)×(d/c), and as will be seen from a comparison between FIGS. 8 and 9, b is smaller and c is larger in comparison with those in the defect detecting inspection, so that the magnification becomes small. The irradiation angle β can also be made small.

In connection with FIG. 1, there have been explained methods of forming high resolution images in the review mode by reducing a beam current, while both the inspection mode and the review mode use a single detector and a single system of a preamplifier to a processing circuit in the A/D converter. On the other hand, as the beam current is reduced, signals detected by the detector are reduced considerably. Consequently, if the amplification factor of the detection system in the review mode is the same as in the defect detecting inspection, an input signal will become as small as the minimum bit or less in the, detection circuit 30, with the result that a satisfactory image is not obtained even if the electron beam is scanned plural times on a sample and the addition of obtained images is performed.

Figure 15:
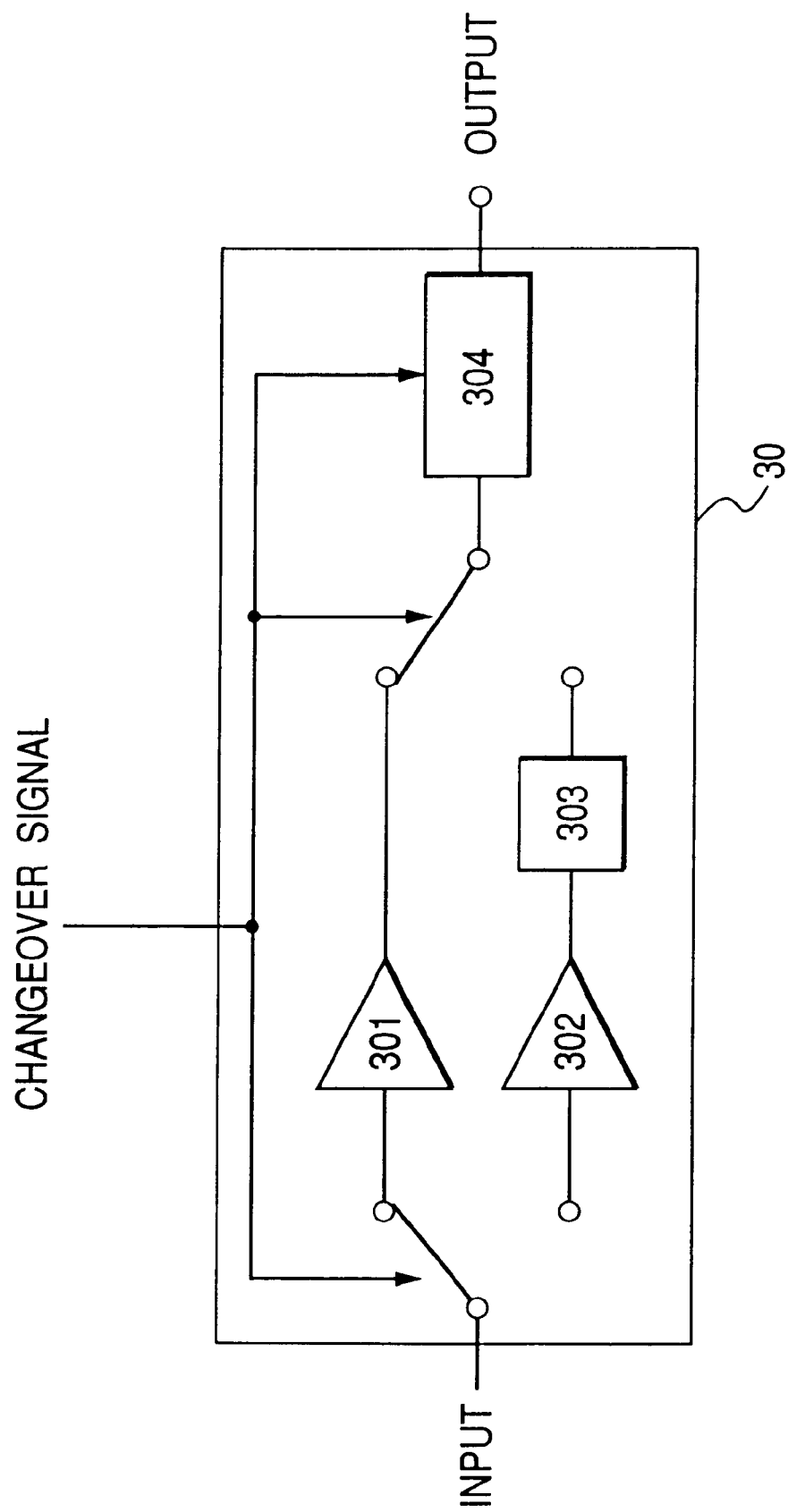
FIG. 15 is a diagram illustrating a configuration of a detection circuit used in Embodiment 1.

In view of this, an additional set of circuits from the preamplifier up to the input to the A/D converter was provided. More specifically, two systems of signal paths are provided in the detection circuit 30 in FIG. 1. This configuration is shown in FIG. 15. In the defect detecting inspection mode, a signal from the detector 9 is inputted directly to an A/D converter 304 via a low-gain amplifier 301. On the other hand, in the review mode, the signal level from the detector 9 lowers because the beam current value decreases. The signal path is switched over to a high-gain amplifier 302 having an amplification factor higher by the amount corresponding to the lowering of the signal level. Further, the signal is passed through a high frequency cut-off filter 303 and is inputted to the AD converter 304. The operation of this circuit will be described below with reference to FIGS. 16(a) and 16(b) which are schematic diagrams of signal waveforms in the defect detecting inspection mode and in the review mode, respectively.

Figure 16A:
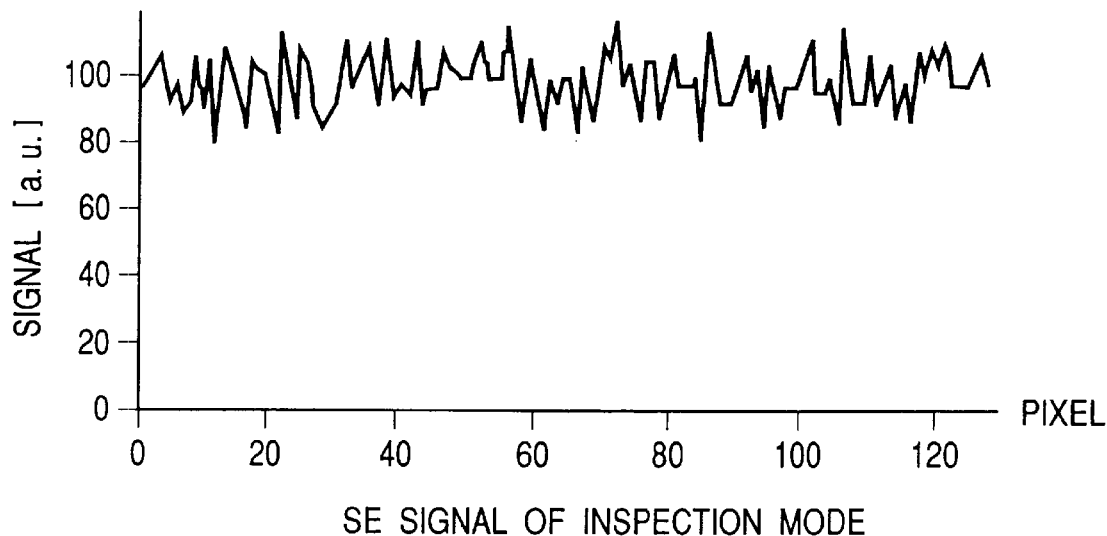
FIGS. 16(a) and 16(b) are diagrams illustrating a signal waveform in a defect detecting inspection and a signal waveform in a review, respectively, in Embodiment 1.

As an example, the beam current in the defect detecting inspection mode is set at 100 nA and that in the review mode is set at 500 pA. The gain ratio between the low and high-gain amplifiers 301, 302 is set at 200 equal to the beam current ratio, and as a result, the average output values of both the amplifiers become equal to each other (100 in arbitrary unit). FIG. 16(a) shows a signal waveform of an image obtained from an area having no pattern on a semiconductor device in the defect detecting inspection mode, and amplitudes of noise are small because a large beam current is used.

Figure 16B:
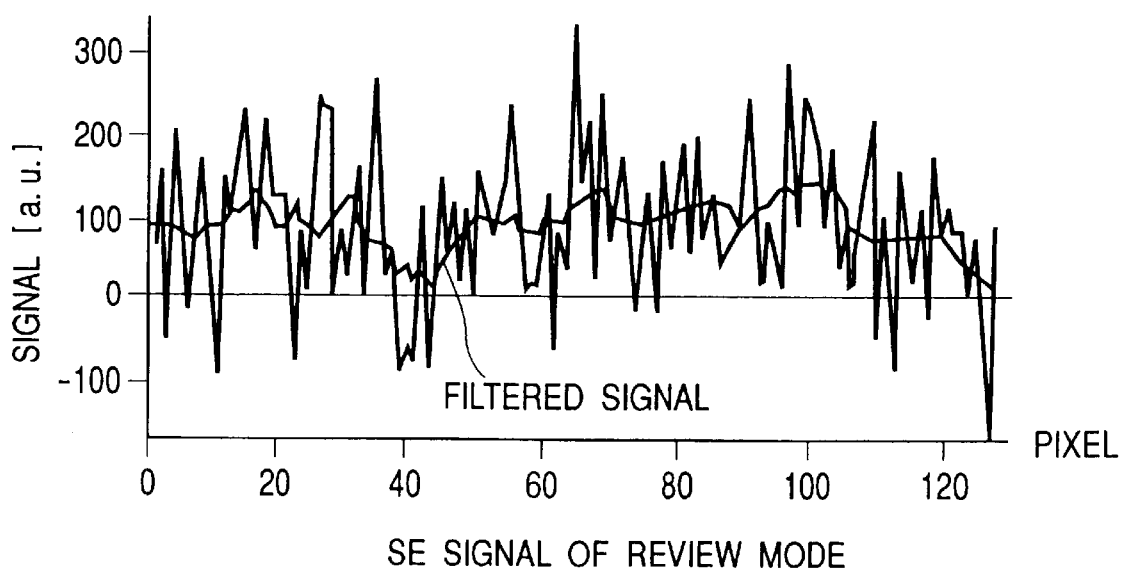

FIG. 16(b) shows a signal waveform of an image obtained from the same area in the review mode. Although the average of the signals is approximately 100, the amplitude of noise is large and the signals swing in a wide range of from −100 to 300 because small signals are amplified with a high gain. If an analog signal swings to a negative value, a digitized value becomes zero. A too large signal exceeds the full scale of the A/D converter. Thus, there arises a problem that an accurate waveform is not obtained even if digital signals are added and averaged.

To solve this problem, the high frequency cut-off filter 303 was placed behind the high-gain amplifier. An input signal to the A/D converter 304 has its noise suppressed as indicated by the waveform "FILTERED SIGNAL" in FIG. 16(b). Further, after digitizing this waveform, if the scanning of electron beam is performed plural times and the obtained signals are added together, there can be obtained an image signal having a satisfactory S/N ratio.

The three methods for improving resolution and the method for solving the problem caused by reducing the beam current have been described above.

In this embodiment, for the improvement of resolution, the third method is mainly adopted in which excitation conditions for the condenser lens are changed, and the first method involving changing the current value extracted from the cathode is adopted as an auxiliary method. Concrete examples of numerical values will be shown below.

Figure 10:
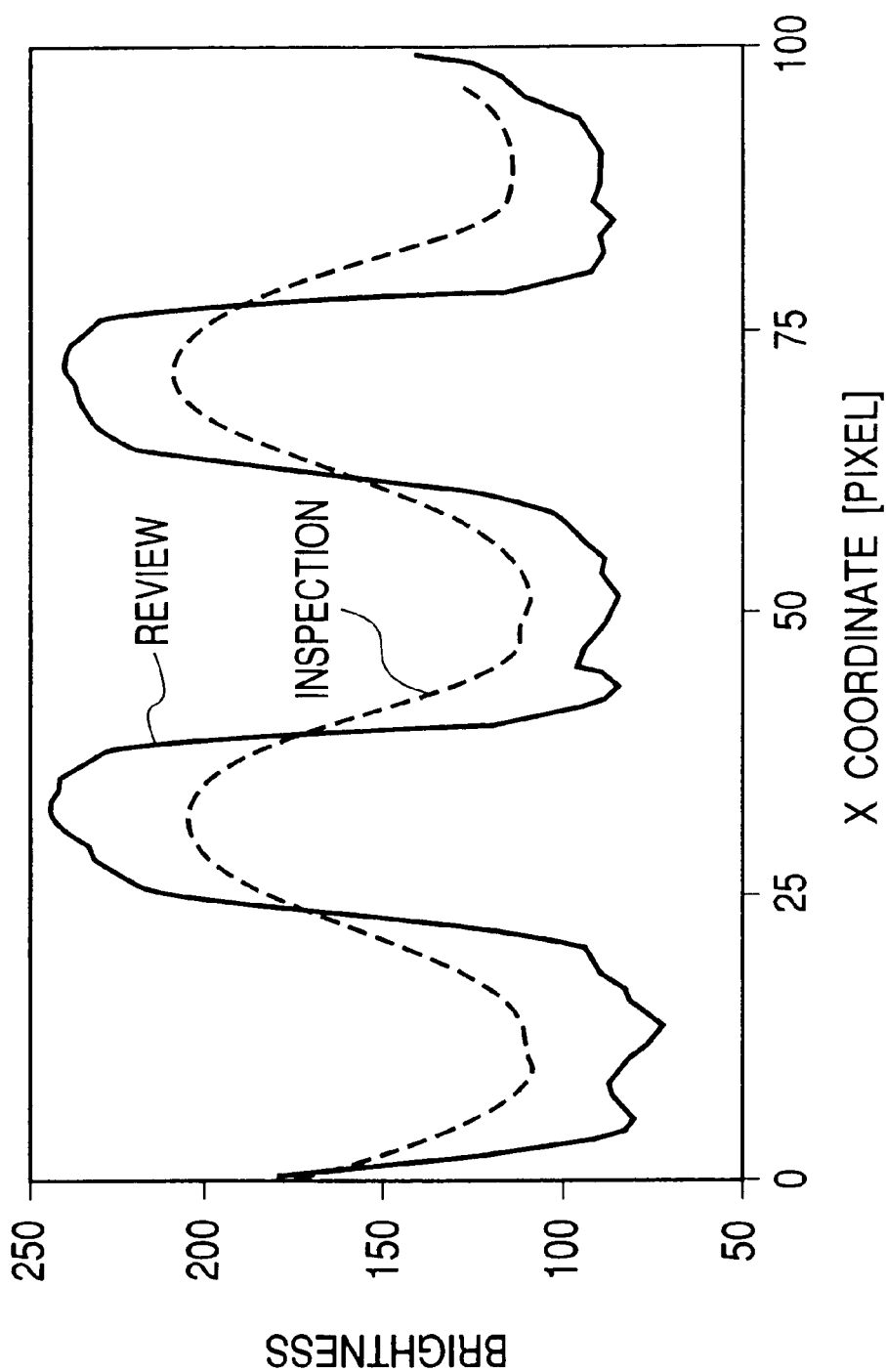
FIG. 10 is a diagram explaining the effect of Embodiment 1.

In the defect detecting inspection mode, the angular current intensity of electrons from the cathode was set at 0.5 mA/sr, the magnification of the optical system was set at 1.0, and the beam current is set at 100 nA. In this conditions, the resolution of the obtained image was approximately 0.08 μm. A line profile of an image of a line and space pattern obtained in the inspection mode is shown in FIG. 10.

In the review mode, the current for the condenser lens was increased and the magnification was set at 0.2 Further, the angular current intensity of electrons from the cathode was reduced to 0.1 mA/sr by controlling the high-voltage power supply of the electron gun. As a result, the beam current was decreased to 500 pA and therefore the, gain of the preamplifier in the detection system was changed to 200 times, employing a filter for reducing a frequency characteristic to about one-tenth. The electron beam scanning speed was set at about one-tenth of that in the defect detecting inspection. Further, the addition of images was conducted 64 times to compensate for the deterioration of the S/N ratio. At this time, the resolution of the obtained image was about 0.02 μm. A line profile of the image is superposed in FIG. 10. It is understood that the line profile in the review mode rises sharply and is larger in amplitude. This fact clearly shows that the resolution is improved and that even a fine object can be observed.

Embodiment 2

Figure 11:
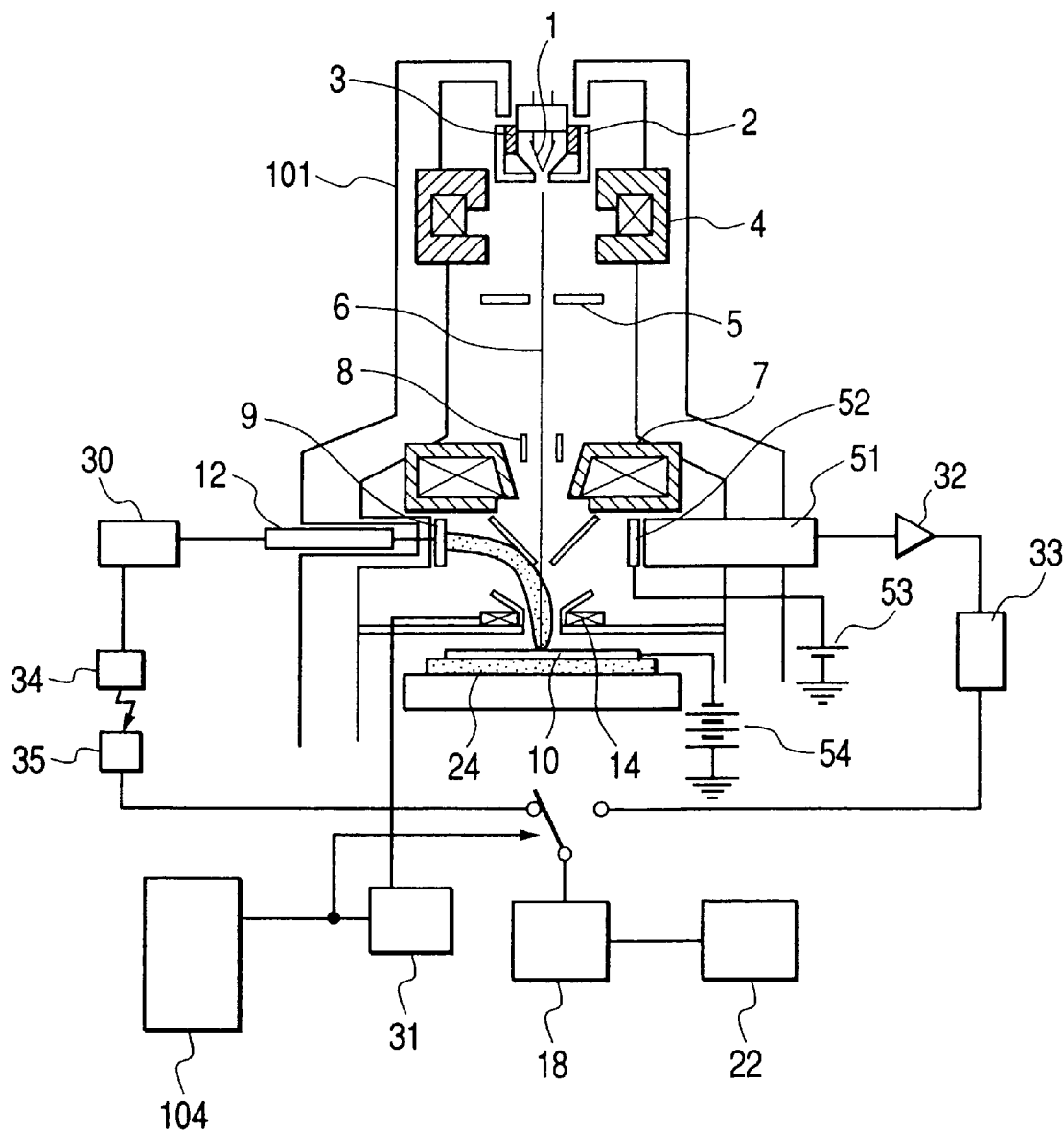
FIG. 11 is a diagram illustrating a configuration according to Embodiment 2 of the present invention.

In Embodiment 1 the same detector was in both the review mode and the defect detecting inspection mode. In the review mode, however, since detected signals are reduced markedly, it is necessary that the gain of the preamplifier 12 be increased to 200 to 1000 times in accordance with the rate of decrease of the electric current. Further, if the gain is increased while keeping the frequency characteristic as high as in the defect detecting inspection, there will arise problems that the circuit oscillates and the amplitude of the noise in the circuit becomes larger than the average of the signals. For this reason it is necessary to add a high frequency cut-off circuit, resulting in complexity of the circuit. As a result, there is a possibility that noise may be introduced into detected signals in the defect detecting inspection or the frequency characteristic may be deteriorated. In this embodiment, to solve this problem, there is provided a detector used exclusively for the review mode. FIG. 11 is a configuration diagram of this embodiment. The detector for the review mode is disposed at a position substantially symmetric with a detector 9 for the defect detecting inspection with respect to the optical axis of the electron beam. This detector is one used in an ordinary type of a scanning electron microscope and is composed of a scintillator 52 and a photomultiplier tube 51. The frequency response characteristic thereof is DC to 20 MHz.

Secondary electrons emitted from a sample 10 are deflected by an ExB deflector 14 toward the detector 9 in the defect detecting inspection, while in the review mode they are deflected toward the detector exclusively for the review. The secondary electrons are irradiated to a converter electrode opposed to the respective detectors, and then secondary electrons emitted from the converter electrode are detected.

To a front side of the scintillator 52 is applied a high positive voltage from a power supply 53, so as to accelerate the secondary electrons, collide them with the front side and thereby convert them into light. The light is multiplied by the photomultiplier tube 51 and is detected.

Change-over of a deflection direction of the secondary electrons is attained by reversing the polarity of a control power supply 31 for the ExB deflector 14 (reversing polarities of the applied voltage and the deflection coil current). Interlocking with this, a signal provided from one of the detectors is displayed on a monitor 22 via a memory 18. This change-over is performed by a control unit 104.

In connection with the construction of Embodiment 2, a more concrete configuration of the optical system will be described below with reference to drawings, which employs an electron gun for generating a large-current electron beam.

First, the configuration of an electron gun optimized for a large current will be explained.

Figure 17:
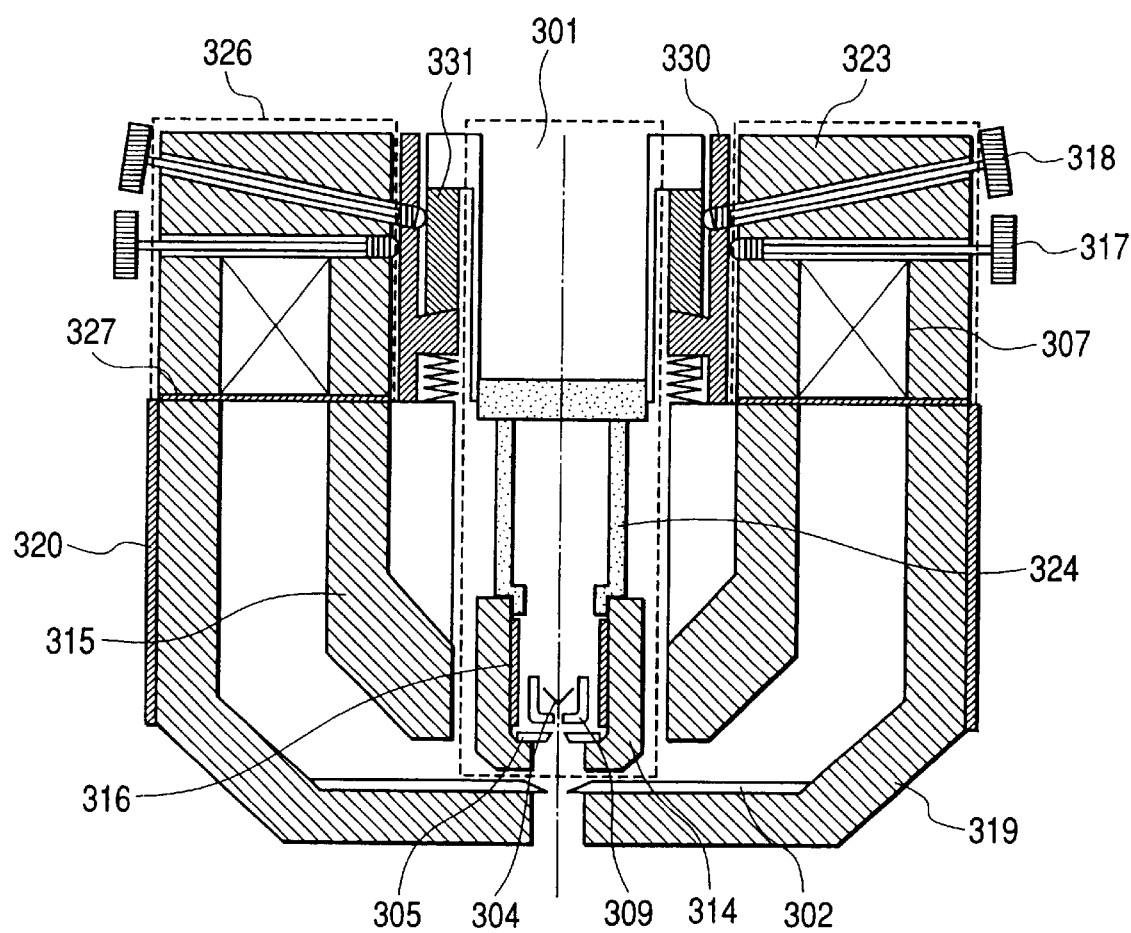
FIG. 17 is a diagram illustrating an electron gun unit in electron optic systems in Embodiments 1 and 2.
Figure 18:
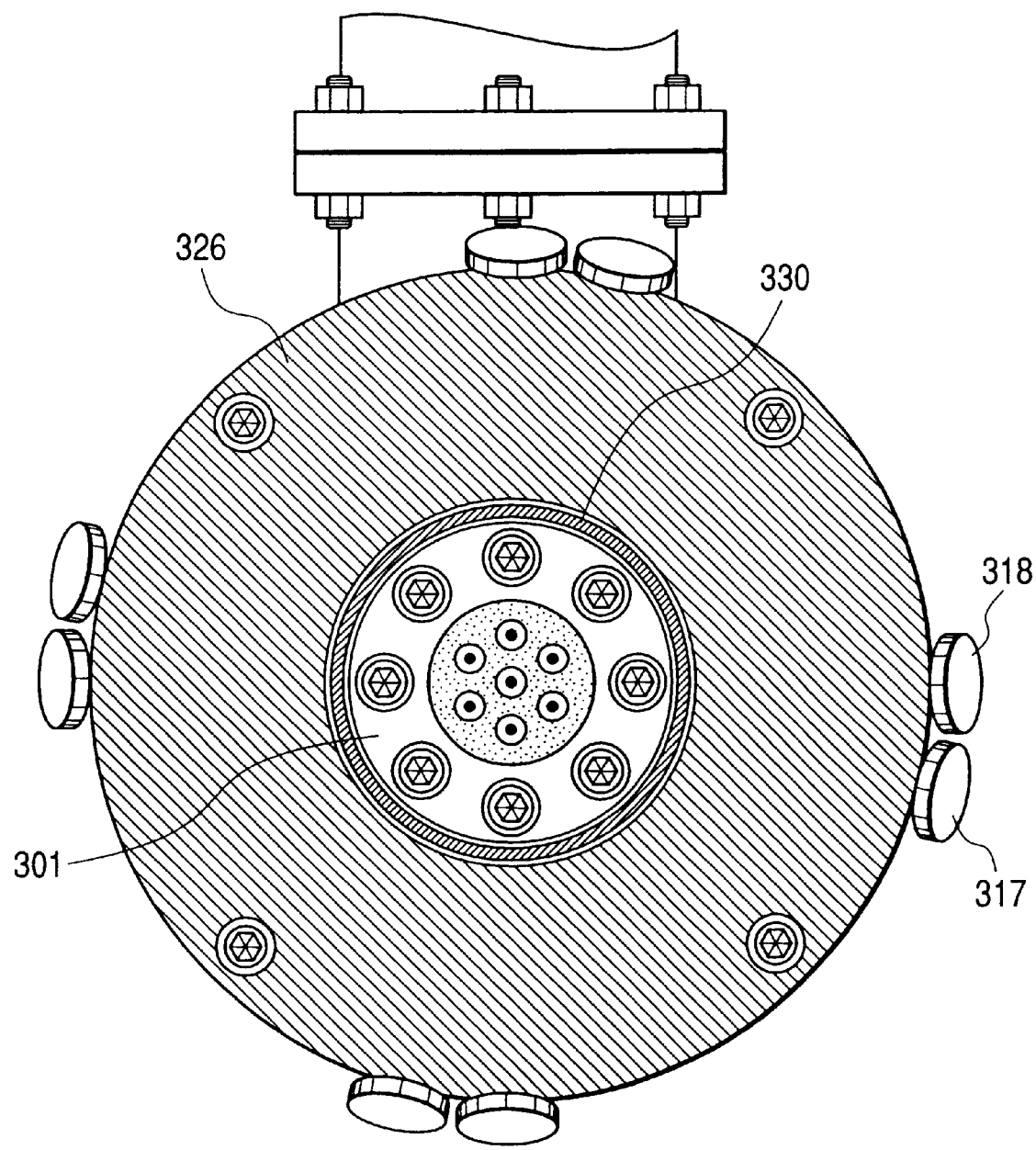
FIG. 18 is a diagram illustrating an electron gun unit in the electron optic systems in Embodiments 1 and 2.

FIG. 17 is a cross-sectional view for explaining an overall configuration of an electron gun for a large current and FIG. 18 is a plan view thereof. The electron gun comprises a head unit 301, a removable coil unit 326, a fixed pole piece 315, a lower pole piece 319, a horizontal adjustment screw 317 of the gun head, a tilt adjustment screw 318 of the gun head, a horizontal moving unit 330, a tilt moving unit 331, and an outer heater 320. The head unit 301 of the electron gun is composed of a cathode 304, a suppressor electrode 309, an extraction electrode 305, a movable pole piece 314, a ceramic insulator 324, and an inner heater 316. The cathode 304, the suppressor electrode 309, the extraction electrode 305, the movable pole piece 314, and the inner heater 316 are suspended from the ceramic insulator 324. The removable coil unit 326 is made up of a coil 307, a pole piece 323, and a coil fixing piece 327. The coil 307 is fixed to the pole piece 323 with the coil fixing piece 327. The removable coil unit 326 is configured such that it can be removed from the electron gun at the time of baking. The movable pole piece 314 and the fixed pole piece 315 are spaced from each other.

The head unit 301 of the electron gun is fixed to the tilt moving unit 331, and the tilt moving unit 331 is seated on a curved surface of the horizontal moving unit 330. The tilt adjustment screw 318 of the gun head is secured to the horizontal moving unit 330 and the horizontal adjustment screw 317 of the gun head is secured to the pole piece 323 of the removable coil unit 326. By pushing the horizontal moving unit 330, the horizontal adjustment screw 317 of the gun head causes the head unit 301 of the electron gun to move in the horizontal direction relatively to the lower pole piece 319. Likewise, by pushing the tilt moving unit 331, the tilt adjustment screw 318 of gun head causes the head unit 301 to tilt with the cathode 304 as a fulcrum.

Figure 19:
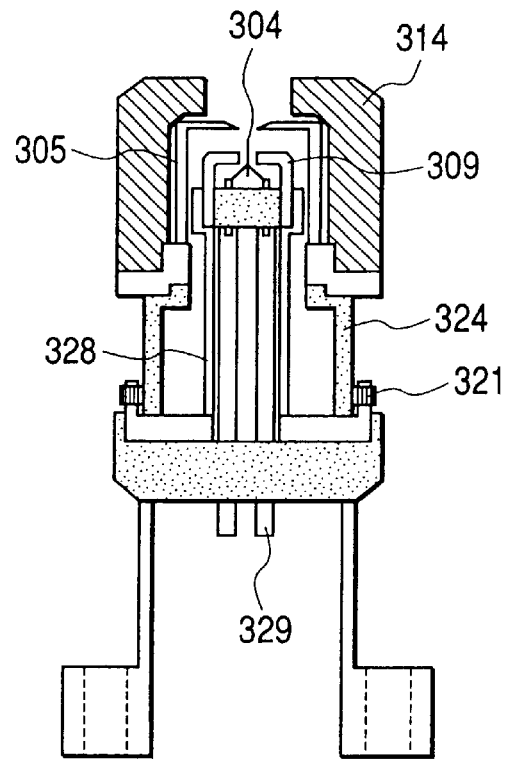
FIG. 19 is a diagram illustrating components of an electron gun used in the electron optic systems in Embodiments 1 and 2.
Figure 20:
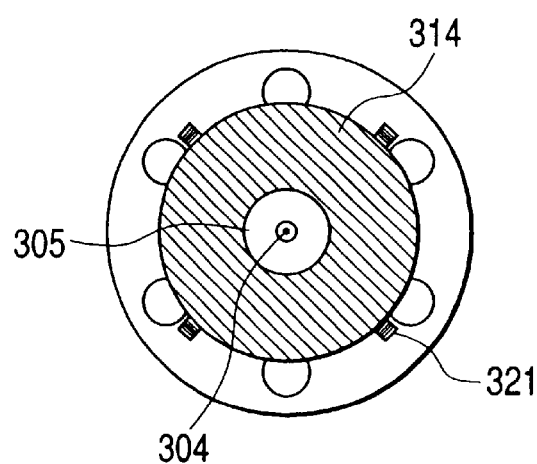
FIG. 20 is a diagram illustrating components of the electron gun used in the electron optic systems in Embodiments 1 and 2.

The following explains a method of centering the cathode 304 and the extraction electrode 305 in the head unit 301 of the electron gun by reference to FIGS. 19 and which are a cross-sectional view and a plan view, respectively, of the head unit of the electron gun. The head unit of the electron gun comprises the cathode 304, suppressor electrode 309, the extraction electrode 305, the movable pole piece 314, the ceramic insulator 324, the alignment screw 321, the pedestal 328 of the suppressor electrode, and the pillar 329 for gun heating. The cathode 304 is fixed to the pillar 329 for gun heating and the suppressor electrode 309 is fixed to the pedestal 328 of the suppressor electrode. The extraction electrode 305 and the movable pole piece 314 are made integral with the ceramic insulator 324, and alignment screws 321 secured to the pedestal 328 of the suppressor electrode fix the ceramic insulator 324 in place.

Alignment of the extraction electrode 305 with respect to the cathode 304 is performed by initially aligning the extraction electrode 305 with the cathode 304 by pushing the ceramic insulator 324 with the alignment screws 321 at the time of mounting the cathode 304 and thereby moving the movable pole piece 314 and the extraction electrode 305 integral with the ceramic insulator 324 in parallel with and relatively to the cathode 304, and then fixing the extraction electrode 305 and the cathode 304 together.

A mechanical alignment of the electron gun is effected by a combination of the operation of aligning the cathode 304 relative to the extraction electrode 305 and the movable pole piece 314, performed at the time of mounting the cathode 304 and the operation of aligning the head unit 301 of the electron gun relative to an anode electrode 302 and the lower pole piece 319, performed by extracting an electron beam. The combination of the two aligning operations makes possible the more accurate alignment of the cathode 304 relative to the electromagnetic lens.

It is necessary to secure such a sufficient distance between the movable pole piece 314 and the fixed pole piece 315 to ensure a sufficient withstand voltage therebetween. However, if this distance is made too large, it becomes impossible to generate a strong on-axis magnetic field and a stronger excitation is required for retaining the same optical conditions of the electron gun Next the withstand voltage between the fixed pole piece 315 and the movable pole piece 314 will be considered.

Suppose that a distance between the fixed pole piece: 315 and the movable pole piece 314 is S (mm), a horizontal shift of the head unit 301 of the electron gun is ±1 (mm), and a tilt of the head unit 301 is ±100 (mrad). The closest possible distance between the fixed pole piece 315 and the movable pole piece 314 after the alignment adjustment is about (S-1.5) (mm). Suppose a guaranteed dielectric strength in the space is 5 (kV/mm), then a guaranteed withstand voltage in the space between the movable pole piece 314 and the fixed pole piece 315 is 5 (S-1.5) (kV).

Figure 21:
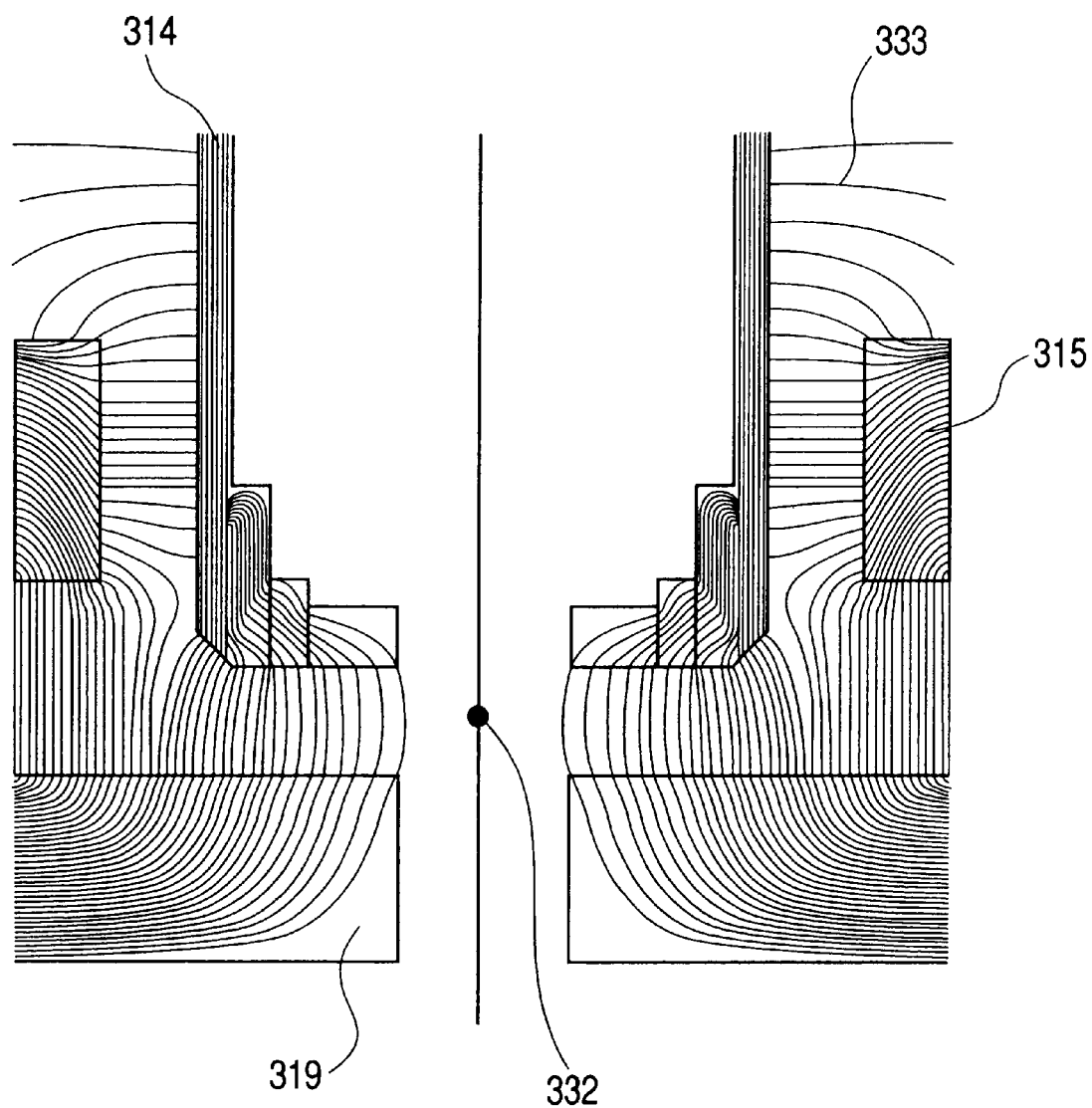
FIG. 21 is a diagram illustrating the operation of the electron gun used in the electron optic systems in Embodiments 1 and 2.

FIG. 21 shows an enlarged view of a calculated magnetic field distribution obtained with a current of 1 (A) provided to the coil 307 of 1000 (T) in the vicinity of the cathode 304 of the above electron gun. FIG. 21 shows magnetic lines of force calculated based upon the movable pole piece 314, the fixed pole piece 315 and the lower pole piece 319, where the inside diameters of the movable pole piece 314 and the lower pole piece are 14 (mm); and a spacing between the pole pieces is 8 (mm). From this result it is seen that even if the distance between the movable pole piece 314 and the fixed pole piece 315 is 8 (mm), a strong on-axis magnetic field can be produced by magnetic coupling in the space therebetween.

The small-sized large-current electron gun structure capable of stable operation has been described above. Next, the following description describes the configuration of an optical system employing this electron gun.

Figure 22:
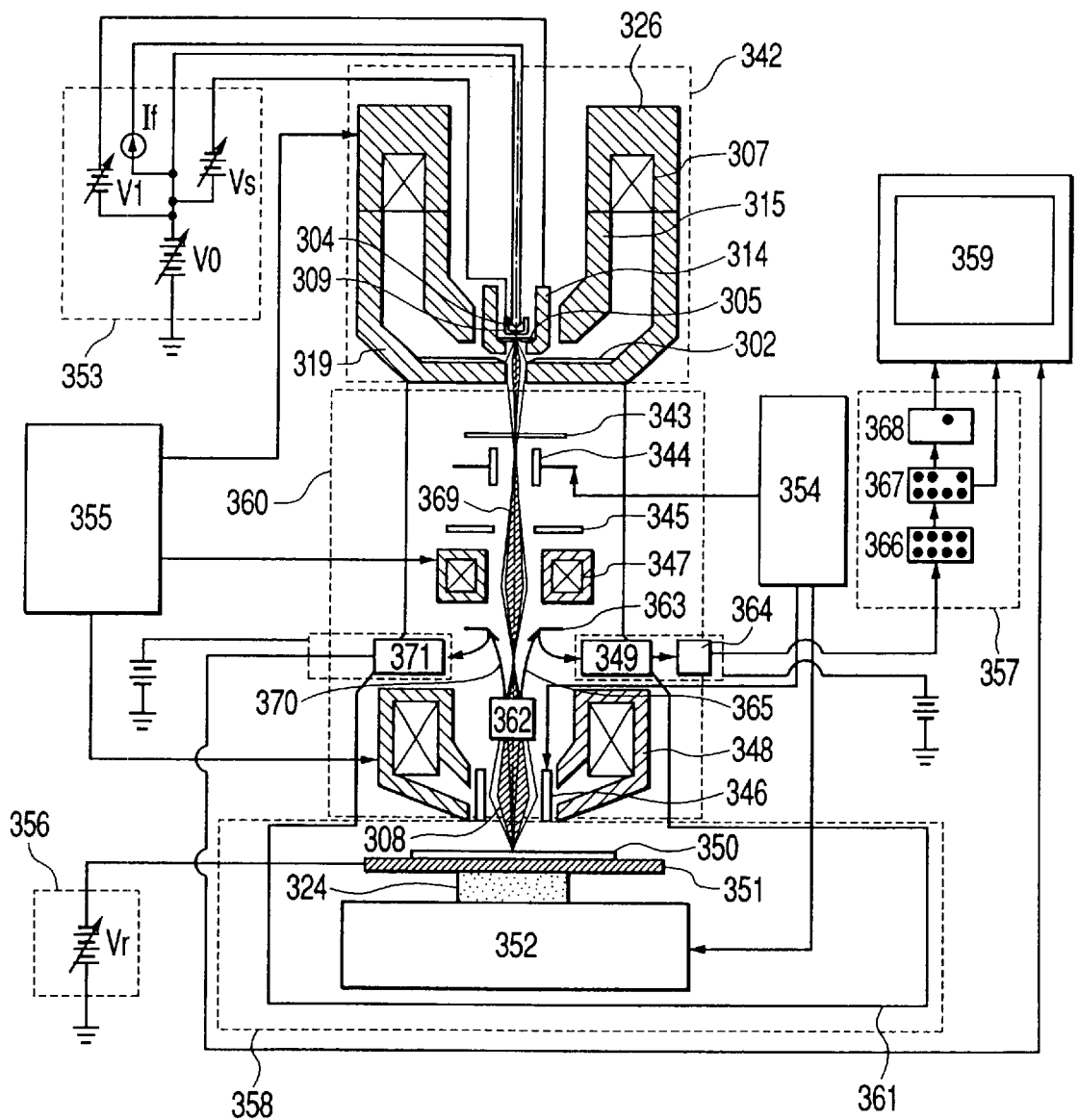
FIG. 22 is a diagram illustrating a concrete configuration of the electron optic system in Embodiment 2.

The electron optic system shown in FIG. 22 comprises an electron gun unit 342, an optics column unit 360, a stage unit 358, an image processing unit 357, a display device 359, a deflection control unit 354, a lens control unit 355, a retarding power supply 356, and a power supply 353 for the electron gun. The electron gun unit 342 is made up of a removable coil unit 326, a coil 307, a fixed pole piece 315, an anode 302, a lower pole piece 319, a movable pole piece 314, an extraction electrode 305, a suppressor electrode 309, and a cathode 304. The cathode 304 is configured so as to be provided with an electric current If for heating from the power supply 353 for the electron gun and a desired acceleration voltage V0. Further, a reverse bias voltage Vs with respect to the cathode 304 is applied to the suppressor electrode 309, and a positive bias voltage V1 is applied to the extraction electrode 305.

The optics column unit 360 is made up of a movable aperture 343, a blanking plate 344, a Faraday cup 345, a condenser lens 347, a semiconductor detector 349, a detector 371, a deflector 346, an objective lens 348, an ExB deflector 362, and a converter electrode 363. The semiconductor detector 349 operates at a sampling frequency of 10 MHz to 200 MHz and is supplied with a high voltage for attracting secondary electrons generated from a sample 350 to the semiconductor detector 349. The detector 371 operates at a sampling frequency up to about 10 MHz and can be supplied with a high voltage like the semiconductor detector 349. The ExB deflector 362 is configured such that the polarities of the electrostatic and electromagnetic deflectors can be reversed between the inspection mode and the review mode.

The stage unit 358 is made up of a sample 350, a sample holder 351, a ceramic insulator 324, a stage driving unit 352, and a sample chamber 361. The sample 350 and the sample holder 351 are electrically insulated from the stage driving unit 352 by the ceramic insulator 324, and are supplied with a retarding voltage Vr.

The cathode 304 has a voltage V0 applied thereto and is supplied with a current If for gun heating, the extraction electrode 305 is supplied with a positive bias voltage V1 with respect to the cathode 304, and the suppressor electrode 309 is supplied with a reverse bias voltage Vs, such that an electron beam. 308 is emitted with an energy V0.

In the inspection mode, the electron beam 308 thus emitted is focused by the magnetic field generated by the removable coil 326 in the electron gun unit 342 to form a crossover between the blanking plates 344. Then, the excitation of the condenser lens 347 is adjusted so that the overall magnification of the optical system becomes 0.5 to 1.5 times and the electron beam is focused onto the sample 350 by the objective lens 348. The amount of a probe current of the electron beam 308 is determined by both the diameter of the movable aperture 343 and the angular current intensity of the electron beam 308 and it is adjustable in the range of from 20 (nA) to 200 (nA). The retarding voltage Vr is applied to the sample 350 from the retarding power supply 356, and is varied to adjust the energy of the incident electron beam 308.

A sawtooth wave of 10 kHz to 200 kHz is generated in the deflection control unit 354 as a deflection signal and thereby the electron beam 308 is deflected by the deflector 346. The deflection control unit 354 controls the stage driving unit 352 so as to move the stage 351 in a direction perpendicular to the direction of the electron beam deflection such that the electron beam 308 scans the sample 350 two-dimensionally. Further, the deflection control unit 354 is configured such that a voltage can be applied to the blanking plate 344 so as to intercept the electron beam 308 by the Faraday cup 345 when the electron beam 308 is not desired to irradiate the sample 350.

The ExB 362 deflector is adjusted such that only secondary electrons 365 generated from the sample 350 are deflected away from the optical axis, then they are irradiated onto the converter electrode 363 and finally attracted to the semiconductor detector 349. The secondary electrons 365 detected by the semiconductor detector 349 are converted into a digital signal by an A/D converter 364, and the digital signal is used to form an image by an image processing unit 357.

The image processing unit 357 calculates a difference image between a reference image 366 picked up initially and an image 367 picked up for comparison at a position different from a position of the reference image 366 on the wafer and transmits the difference image to the display device 359 as a defect-indicating image 368. Also the image processing unit 357 can transmit the image 367 picked up for comparison and containing a defect to the display device 359.

For example, suppose that this SEM type circuit pattern inspecting instrument inspects a wafer containing a pattern size of 0.1 ($\mu$m), then it is preferable that the probe size is equal to or less than 0.1 ($\mu$m) on the sample 350.

In the case of performing the above inspection under the conditions that the focal length of the objective lens 348 is 30 to 40 (mm) and the probe current is 50 (nA) to 150 (nA), it is essential that the total magnification of the optical system is in the range of 0.5 to 1.5 for suppressing chromatic aberration of the objective lens 348, and consequently, it is necessary to suppress aberration of the electron gun.

In the case of conducting the inspection with a conventional electron gun incapable of handling a large electric current, chromatic aberration and spherical aberration of the electron gun as defined on an object side are as large as 45 (nm) to 60 (nm) and 35 (nm) to 50 (nm), respectively, and consequently, the probe size on the sample 350 becomes 0.15 ($\mu$m) to 0.3 ($\mu$m).

When the electron gun according to the present invention is used with an acceleration voltage of 10 (kV) and an excitation of 800 (AT) to 1000 (AT), there can be attained a focal length of the electron gun of 8 (mm) to 11 (mm) as defined on the object side, and therefore chromatic aberration and spherical aberration of the electron gun as defined on the object side become 15 (nm) to 20 (nm) and 1 (nm) to 2 (nm), respectively, and as a result, a probe size of 0.05 ($\mu$m) to 0.1 ($\mu$m) is attained on the sample 350.

Further, when the electron gun of the invention is used with a magnification of 5 to 10 and the reducing optical system for reduction to 0.1 to 0.5 is formed of the condenser lens 347 and the objective lens 348, influences by contaminants adhering to the blanking plate 344, the movable aperture 343, and the Faraday cup 345 are reduced. For example, suppose that an image drift of 0.5 ($\mu$m) is caused by contaminants when all the lenses are used to provide a magnification of 1, adoption of the above optical conditions reduces the drift to 0.05 ($\mu$m) to 0.1 ($\mu$m).

On the other hand, for confirming a detected defect on a circuit pattern by forming a sharp high-resolution image of the defect, the defect image is observed with the optical conditions being set for the review conditions. In the review conditions, the excitation of the coil 307 is adjusted so that an electron beam 369 forms a crossover above the movable aperture and the probe current becomes 100 (pA) to 5 (nA). Further, the excitation of the condenser lens 347 is adjusted so that the overall magnification of the optical system becomes 0.2 to 0.3 and the electron beam is focused onto the sample 350 through the objective lens 348. Secondary electrons 370 generated from the sample 350 are detected by a detector 371 by using the ExB deflector 362 with its polarity reversed from that for the inspection mode. The detected secondary electrons 370 are imaged on the display device 359.

A stable inspection instrument capable of switching between the inspection and review conditions instantly and handling a large electric current is realized by mounting the electron gun of the invention on an SEM type circuit pattern inspecting system provided with the review function and by adjusting the electron gun as described above.

Embodiment 3

In case of some particular kinds of defects, a contrast of an image of the detected defects may disappear if the conditions for the review mode have not been set appropriately. For example, the contrast of an image of some defects in interconnections by via holes disappear after the irradiation of an electron beam is repeated several times. Therefore the number of times of addition of images needs to be limited when such defects are observed in the review mode, and as a result, an electron beam current needs to be made rather large to obtain images of a satisfactory S/N ratio.

For some kinds of defects, in the defect detecting inspection mode using a large-current electron beam, the stronger the retarding electric field (the electric field applied to a wafer to be inspected for decelerating the electron beam), the larger the contrast of the image of defects, but, on the other hand, when a small electron beam current is used, the weaker the retarding electric field, the more enhanced the contrast of the image of the defects.

As an example, the following explains a method of setting the conditions for the review mode when a defective interconnection is observed.

A semiconductor manufacturing process includes a process step of forming connection holes and embedding an electrically conductive material into the connection holes for through connections between laminated upper and lower layers. Defective formation of the connection holes or defective embedment of the material causes a complete electrical disconnection or a very high resistance. When the defect detecting inspection is performed in the process step for producing the interconnections, embedded holes having good electrical conduction appear bright and non-conductive embedded holes appear dark.

Further, embedded holes having marginal electrical conduction appear intermediate between bright and dark and are detected as defects when they are compared with the embedded holes having perfect conduction. The embedded holes having marginal electrical conduction come to appear as bright as those having perfect conduction after several tens of addition of images are performed with reduced electrical current in the review mode, and usually the review does not provide any useful information.

In view of the above fact, in the defect detecting inspection for connection holes, the brightness level of each detected defect is stored in a memory in combination with coordinates of the defect, and in the subsequent review mode for the gray defect, the optical conditions are set automatically such that the beam current does not become equal to or less than 5 nA and the number of times of addition of images is limited to ten. On the other hand, in the review mode for very dark defects, the beam current is set as low as possible and is limited to 500 pA.

The above is just an example. The point is that defects are classified automatically using information obtained from the images in the defect detecting inspection such as brightness of the images, defect sizes and defect shapes and then are automatically correlated. with the suitable optical conditions for the review mode such as a scanning area, a beam current, a scanning speed, and the number of times of addition of images. In the present invention, mechanical movements such as the movement of the aperture are eliminated to the utmost in changing of the optical conditions, and consequently, the optical conditions can be changed in an instant depending upon defects.

Embodiment 4

Figure 12:
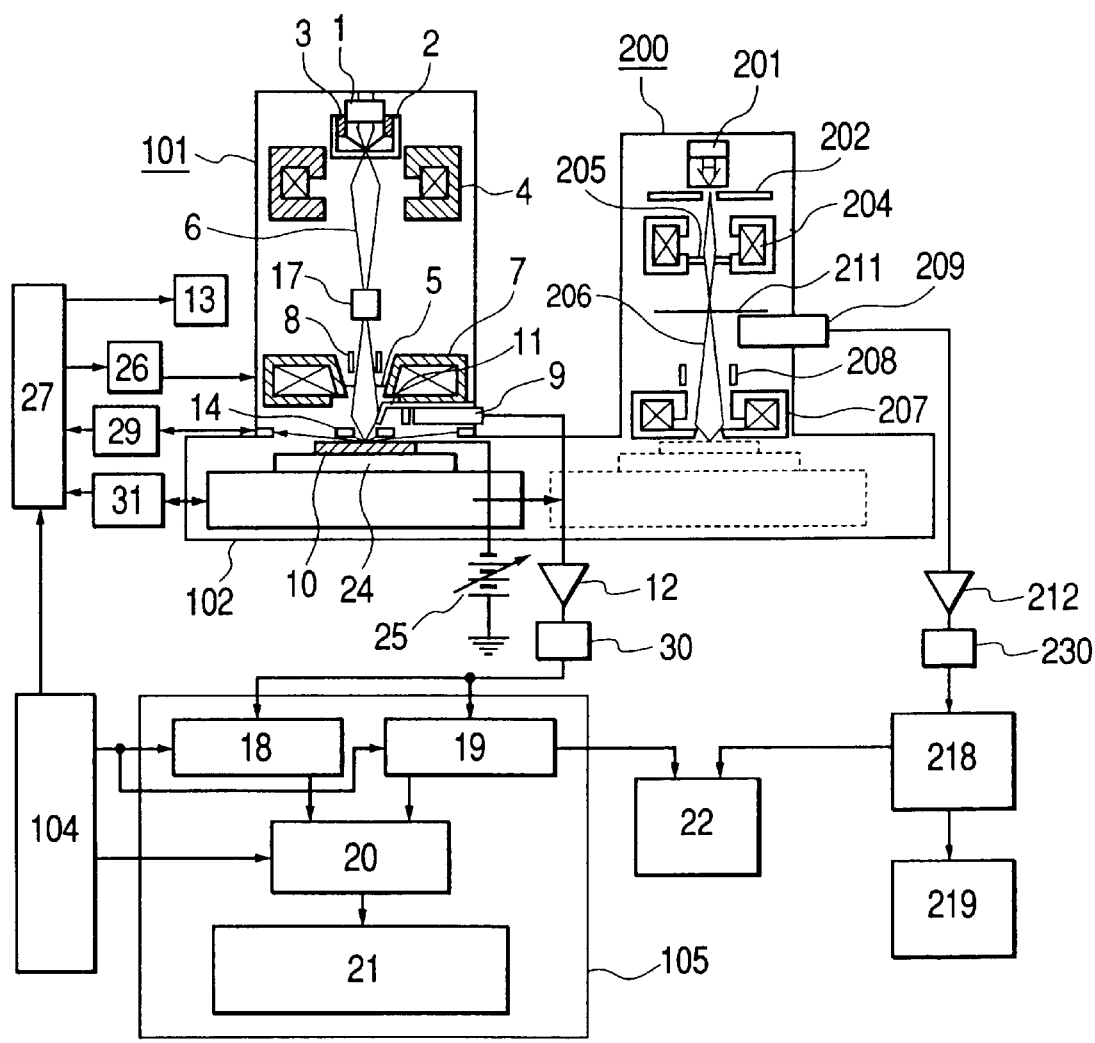
FIG. 12 is a diagram illustrating a configuration according to Embodiment 3 of the present invention.

In this embodiment an electron optic system for the review mode is separated from an electron optic system for the defect detecting inspection. A more detailed description will be given below with reference to FIG. 12, which is a configuration diagram of this embodiment.

An inspection instrument of this embodiment is roughly divided into an electron optic system 101 for the defect detecting inspection, an electron optic system 200 for the review, a sample chamber 102, a control unit 104, and an image processing unit 105. The components other than the electron optic system 200 for the review are substantially the same as in Embodiment 1.

The electron optic system 200 for the review is made up of a cathode 201, an electron beam extraction electrode a 202, a condenser lens 204, a scanning deflector 208, an aperture 205, and an objective lens 207. A secondary electron detector 209 is disposed above the objective lens 207 and an output signal from the secondary electron. detector 209 is amplified by a preamplifier 212 and is transmitted to a low-speed image display circuit 218.

A retarding voltage is applied to a stage 24. When the stage is moved from below the electronic optic system 101 for the defect detecting inspection to below the electronic optic system for the review, it is sometimes preferred, depending on the structure of the stage, that the stage is moved after once disconnecting the stage from the retarding voltage. Therefore, an appropriate selection may be made in view of the retarding voltage applied and the type of a substrate to be inspected.

The following describes the points of this embodiment which are the specifications, differences and features of the electron optic system for the review and the electron optic system for the defect detecting inspection.

The electron optic system 101 for the defect detecting inspection can acquire images at a very high speed so as to perform the inspection of the entire wafer surface in a practical period of time. The time required for forming an image of 100 $\mu$m square with a pixel size of 0.1 $\mu$m is equal to or less than 20 msec. The stage is moved continuously for obtaining images at a high speed and the electron beam is scanned in a direction perpendicular to the moving direction of the stage. The inspection instrument was designed so as to provide a beam current of at least 20 nA for realizing a high-speed image formation with an S/N ratio sufficient for the inspection. To be more specific, the angular current intensity obtained from a cathode 1 was set at about 1 mA/sr which is a stably-obtainable limit value and is about twenty times as large as that of a high-resolution SEM. Further, a lens aperture is made larger compared with that in the high-resolution SEM and the beam taking-in angle α for the electron beam emitted from the cathode 1 (i.e., a beam divergence half-angle of a portion of the electron beam emitted from the cathode 1 at a wide angle which irradiates a sample 10) was set at about 20 times larger.

If an image is distorted at its periphery or image resolution at the periphery of the image is deteriorated compared with that at the central portion of the image, the inspection sensitivity becomes non-uniform, so it is necessary that the area scanned by the electron beam is more than enough. For this reason, the focal length and the operational distance of an objective lens were made considerably longer than those of an ordinary type of a high-resolution SEM.

With an increase of the entrance half-angle β of the electron-beam irradiating a sample, the depth of focus becomes smaller. Since the angle β is the angle α divided by the overall magnification M of the entire optical system, the magnification M cannot be made so small and therefore the magnification M is made fairly larger compared with that of the high-resolution SEM.

With the above design, a large electric current necessary for a high speed imaging can be obtained while ensuring the resolution required for the defect detecting inspection. In, this electron optic system, as noted above, it is apparent from the magnification of the optical system and the focal length and the operational distance of the objective lens that, even if the electron beam current is simply reduced, the same resolution as that of the high-resolution SEM cannot be obtained.

In the electron optic system for the review, high-speed operation is not so important. Besides, since the coordinates of a area to be observed are already known accurately, the field of view having 20 μm suffices. Therefore, the electron beam current may be set small. Moreover, the focal length and the operational distance of the objective lens may be made short and the magnification of the optical system can be set small. From these points it is possible to obtain an image having the same high-resolution as in the ordinary high-resolution SEM.

A description will now be given of the electron optic system 200 for the review. As the cathode 201 there was used a Zr/O/W type cathode which is a diffusion-supply type thermionic field-emission (Schottky emission) cathode similar to that used in the optical system for the defect detecting inspection. As the angular current intensity is increased, the energy width of emitted electrons also increases and so does a chromatic aberration. Since the beam current in the electron optic system for the review may be set equal to or less than 100 pA, the angular current intensity was set equal to or less than 0.05 mA/Sr. As a result, the energy width of the electron beam 206 decreases to about one-third to one-fourth of that in the electron optic system for the defect detecting inspection and chromatic aberration so much decreases. The electron beam 206 is extracted from the cathode 201 by applying a voltage to the extraction electrode 202. The electron beam 206 can be accelerated by applying a high negative voltage to the cathode 201. In the optical system 200 for the review, the acceleration voltage can be varied in the range of 500V to 10 kV. In the optical system 200 for the review, since a small electric current will suffice, chromatic aberration is small as noted above and the Coulomb effect can be ignored. Thus, since a sufficiently small beam diameter can be obtained with a low acceleration voltage, the acceleration voltage was set at 2 kV as a standard value.

The electron beam 206 travels toward the stage 24 with an energy of 2 kV, is focused by the condenser lens 204, then is focused into a finer beam by the objective lens 207, and is irradiated onto the substrate 10 to be inspected (e.g., a wafer or a chip) on the stage 24.

The objective lens 207 is disposed in close proximity to the substrate 10 and the operational distance thereof was set at 5 mm. A focal length of the objective lens is 8 mm. As a result, there could be realized an objective lens of small aberration. The resolution depends mostly on chromatic aberration. Thus, in comparison with the objective lens for the defect detecting inspection, an aberration coefficient is about one-fourth, the energy width of the electron beam is about one-third of that in the optical system for the defect detecting inspection, and therefore the resolution is about one-twelfth. The substrate 10 to be inspected is common to both the defect detecting inspection and the review and therefore a negative voltage can be applied from a high-voltage power supply 25. By adjusting the high-voltage power supply 25, the irradiation energy of the electron beam onto the substrate 23 can be adjusted to an optimum value. Since images of different contrasts can be obtained by changing the irradiation energy, it is possible to obtain various information such as information on whether a detected defect is caused by a difference in shape or in material, or by an electrical conduction.

For formation of images, the electron beam 206 is scanned two-dimensionally with the stage 24 being fixed. secondary electrons generated by the electron beam 206 irradiated onto to the substrate 10 are accelerated by the voltage applied to the substrate 10 as is the case with the optical system 101 for the defect detecting inspection.

Since the objective lens 207 is disposed as close as below about 30 mm to the substrate 10, the detector 209 is disposed above the objective lens 207, and the secondary electrons is passed through the center of the objective lens 207. Since the voltage applied to the substrate 10 is lower as compared with that in the optical system 101 for the defect detecting inspection, the energy of the secondary electron is small, but it is still difficult to draw in the secondary electrons directly into the detector 209. Therefore, the secondary electrons are irradiated onto a converter electrode 211 and the resulting secondary electrons are detected by the detector 209. As the detector 209 there was used a detector comprising a phosphor and a photomultiplier tube which are used in the conventional SEM. A secondary electron signal thus detected is amplified by the preamplifier 212 and is A/D-converted by an A/D converter 230, then the resulting digital signal is displayed on a display monitor 22 for image observation and, if necessary, it is stored as an image file in an external storage 219 such as a disc or can be printed out.

The numerical values of various functions referred to above in Embodiment 4 are only examples. What is essential in this embodiment is that the electron optic system for the review capable of attaining a beam diameter about one-tenth of that in the electron optic system for the defect detecting inspection is arranged side by side in the same sample chamber for the electronic optic system for the defect detecting inspection and that the defect detecting inspection mode and the review mode can be changed over from each other quickly by only a parallel movement of the stage.

Embodiment 5

Figure 13:
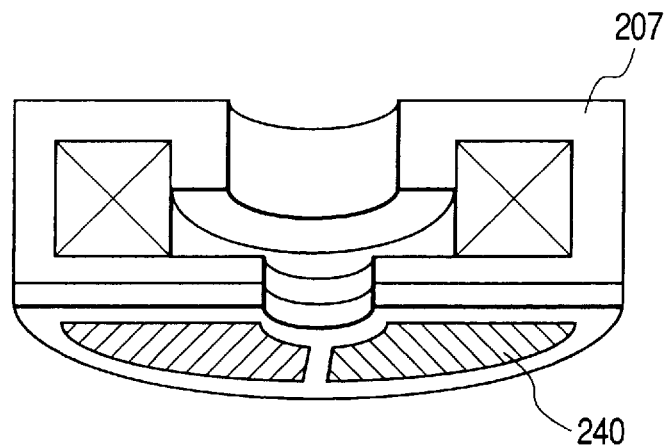
FIG. 13 is a diagram illustrating a configuration according to Embodiment 4 of the present invention.

In this fifth embodiment, an X-ray detector 240 is installed in a lower magnetic path of the objective lens 207 in the electron optic system 200 for the review used in Embodiment 4 so as to detect characteristic X-rays generated by the irradiation of an electron beam. As a result, it became possible to make EDX (Energy-Dispersive X-ray) analysis and hence possible to identify the material of a defect in the review mode. FIG. 13 illustrates the objective lens and the vicinity thereof with an annular X-ray detector incorporated therein, the detector having a central hole.

Alternatively, the operational distance of the objective lens maybe made somewhat larger than in Embodiment 1 and an X-ray analyzer may be inserted between the objective lens and the sample.

Embodiment 6

In the inspection using an electron beam, not only a defect of a shape but also electrical conduction and non-conduction can be inspected. This is because a conductive portion is not charged with electricity and only a non-conductive portion is charged electrically, so that the energy and trajectories of resulting secondary electrons changes and the brightness of the image differs.

This results in generation of a particularly large contrast upon irradiation of a large-current electron beam. But in the electron optic system for the review, the difference in electric charging is small because of a small electric current in the electron optical system for the review and a contrast difference is difficult to appear.

Figure 14:
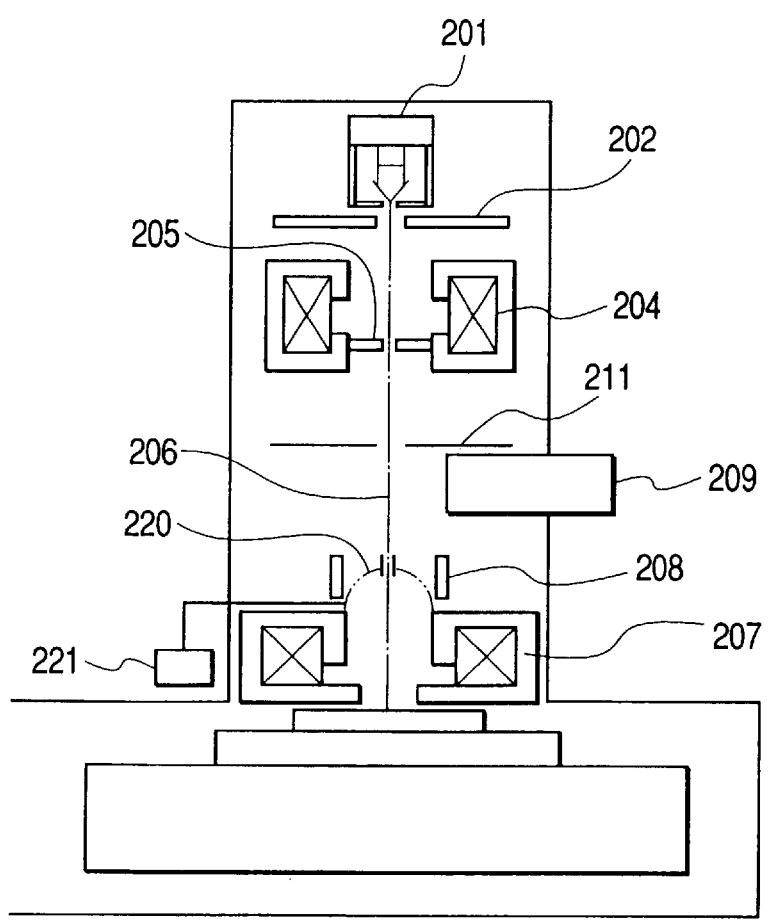
FIG. 14 is a diagram illustrating a configuration according to Embodiment 5 of the present invention.

In view of this point there was provided a secondary electron energy filter capable of filtering even a slight difference in the energy of secondary electrons with a high sensitivity. The energy filter was disposed above the object lens. This analyzer is illustrated in FIG. 14. A semi-spherical mesh 220 is disposed above an objective lens 207 so as to block the trajectories of secondary electrons. Centrally of the mesh 220 is formed a hole for passing a primary electron beam 206. A voltage of about ±20V with respect to the potential of the substrate 10 to be inspected is applied to the mesh 220, whereby the state of electric charging of the substrate can be imaged. The secondary electrons have an energy distribution peaking at about 2 eV with respect to the potential $\phi$ of the position for emitting secondary electrons. Thus, the energy peak of the secondary electrons with respect to ground potential is $(-\phi+2)$ eV.

For example, if a retarding potential of 500V is applied to the substrate 10, the peak of the secondary electron energy becomes 502 eV. If a primary electron beam irradiates an area which is made locally non-conductive by a defect in a pattern and which is otherwise electrically connected to the substrate 10, the area is charged negatively, and consequently, the energy of secondary electrons emitted from the area is higher by the amount corresponding to a potential generated by charging. Suppose the potential generated by charging is 5 V, then the energy of the secondary electrons is 507 eV. Therefore, if a voltage of −505V is applied to the mesh 220, most of secondary electrons from an uncharged area cannot pass the mesh 220, and consequently, only the charged area appears in an image. In this way even a slightly charged area can be detected as a contrast difference.

Although only the case of negative charging has been described here, the mechanism of electric charging by the irradiation of an electron beam in an actual semiconductor device is complicated and there sometimes occurs a positive charging. In such a case, the voltage applied to the mesh 220 may be made equal to or somewhat positive with respect to the retarding potential. In this case, a positively charged area appears dark and the remaining area appears bright.

Resolution of about 0.1V can be obtained by the energy analyzer of this embodiment. In the review, therefore, even if the amount of charging at a defective portion is small due to a small electron beam current, it is possible to, easily identify the defect because the contrast produced by a potential is enhanced.

The present invention configured as above provides the following advantages.

Acquisition of an image signal with a sufficient S/N ratio and efficient setting of the inspection conditions are realized by providing a detection circuit with two processing circuit paths independently optimized for the defect detecting inspection by the high-speed acquisition of images for detecting the presence of defects over a relatively wide area and the review by observing visually an image of a specific narrow portion detected by the defect detecting inspection, respectively. As a result, not only speed-up of the inspection process could be attained but also the results of the inspection became more reliable.

Moreover, a first electron optic system for the defect detecting inspection and a second electron optic system exclusive for the review by observing a specific narrow portion detected by the defect detecting inspection are disposed side by side within a single vacuum vessel and the defect detecting inspection mode and the review mode can be changed over from one another by a mere movement of a sample-carrying stage, and consequently this combination makes possible a quick and highly reliable inspection.

Also, the inspection system of the present invention is provided with a first detector for detecting the presence of a defect, a second detector exclusively for review by observing a specific narrow portion detected by the first detector, and a deflector circuit which directs back-scattered electrons or secondary electrons generated from a sample irradiated by an electron beam to the first detector in the defect detecting inspection and directs the back-scattered electrons or secondary electrons to the second detector in the review, and consequently, this inspection system makes possible a highly reliable inspection using a signal with reduced noise and reduced deterioration of its high frequency characteristics.

What is claimed is:

1. A circuit pattern inspecting instrument comprising:

a cathode for emitting an electron beam;

a stage for mounting a sample thereon;

an electron-optical system for focusing the electron beam;

a deflector for scanning the electron beam on the sample;

a detector for detecting secondary charged particles from the sample irradiated by the electron beam; and a mode setting unit for switching between a first mode and a second mode;

wherein in the first mode, a current of the electron beam is set to a first value and the electron beam is scanned at a first speed;

wherein in the second mode, the current of the electron beam is set to a second value smaller than the first value and the electron beam is scanned at a second speed lower than the first speed; and wherein the circuit pattern inspecting instrument is configured so that first the sample is observed in the first mode, then a particular position on the sample is selected based on image data produced by an output of the detector in the first mode, and then the particular position on the sample is observed in the second mode.

2. A circuit pattern inspecting instrument according to claim 1, wherein an area scanned by the electron beam in the second mode is smaller than an area scanned by the electron beam in the first mode.

3. A circuit pattern inspecting instrument according to claim 1, wherein an image in the second mode is formed using a size of a pixel serving as a minimum picture unit which is smaller than a size of a pixel in the first mode.

4. A circuit pattern inspecting instrument according to claim 1, wherein an electron beam spot on the sample produced by the electron beam in the second mode is smaller than an electron beam spot on the sample produced by the electron beam in the first mode.

5. A circuit pattern inspecting instrument according to claim 1, wherein the electron-optical system includes
an objective lens located closest to the sample, and
a second lens disposed on a cathode side of the objective lens; and
wherein in the second mode, the second lens is adjusted to provide a small magnification of the electron-optical system.

6. A circuit pattern inspecting instrument according to claim 1, wherein the electron-optical system includes a diaphragm having a plurality of apertures having different diameters;
wherein one of the apertures is used in the first mode;
wherein another one of the apertures is used in the second mode; and
wherein the diameter of the aperture used in the second mode is smaller than the diameter of the aperture used in the first mode.

7. A circuit pattern inspecting instrument according to claim 5, wherein the second lens is a condenser lens; and
wherein in the second mode, a position of a crossover formed by the electron beam is shifted.

8. A circuit pattern inspecting instrument according to claim 1, wherein in the second mode, a length of a side of an area scanned by the electron beam is reduced to half or less of a side of an area scanned by the electron beam in the first mode.

9. A circuit pattern inspecting instrument according to claim 1, further comprising:
an image-forming circuit for forming an image by adding image signals obtained by scanning the electron beam a plurality of times;
an image-difference detection circuit for detecting an image difference between a reference image and an image obtained in the first mode; and
a circuit for changing, in the second mode, a magnification of the electron-optical system, a current of the electron beam, a scanning speed of the electron beam, and a number of times of adding image signals in the image-forming circuit in accordance with an output obtained in the first mode from the image-difference detection circuit.

10. A circuit pattern inspecting instrument comprising:
a first electron-optical system including
a first cathode for emitting a first electron beam,
a first objective lens having a first focal length for focusing the first electron beam on a sample positioned at a first sample position, and
a first scanning deflector for scanning the first electron beam on the sample positioned at the first sample position;
a first detector for detecting secondary charged particles generated from the sample positioned at the first sample position;
a second electron-optical system including
a second cathode for emitting a second electron beam,
a second objective lens having a second focal length shorter than the first focal length for focusing the second electron beam on a sample positioned at a second sample position, and
a second scanning deflector for scanning the second electron beam on the sample positioned at the second sample position;
a second detector for detecting secondary charged particles generated from the sample positioned at the second sample position;
an image-forming device for imaging the sample positioned at the first sample position based on an output of the first detector, and for imaging the sample positioned at the second sample position based on an output of the second detector; and
a stage for moving a sample between the first sample position and the second sample position;
wherein the first electron-optical system, the second electron-optical system, the first detector, the second detector, and the stage are housed in a single vacuum chamber; and
wherein the circuit pattern inspecting instrument is configured so that
first the sample is observed at the first sample position with a current of the first electron beam being set to a first value and the first electron beam being scanned at a first speed,
then a particular position on the sample is selected based on image data produced by an output of the first detector,
then the particular position on the sample is moved to the second sample position by moving the stage, and
then the particular position on the sample is observed by enlarging the particular position on the sample using the second electron-optical system with a current of the second electron beam being set to a second value smaller than the first value and the second electron beam being scanned at a second speed slower than the first speed.

11. A circuit pattern inspecting instrument according to claim 10, wherein the first electron beam irradiates a wider area on the sample than does the second electron beam.

12. A method of inspecting a circuit pattern comprising the steps of:
(a) detecting, using a first detector disposed at a first position, secondary charged particles from a sample mounted on a stage and irradiated by a first electron beam scanning the sample at a first scanning speed with a current of the first electron beam being set to a first value; and
(b) detecting, using a second detector disposed at a second position different from the first position, secondary charged particles from a particular position on the sample irradiated by a second electron beam scanning the sample at a second scanning speed lower than the first scanning speed with a current of the second electron beam being set to a second value lower than the first value, the particular position being selected based on an output of the first detector.

13. A method of inspecting a circuit pattern comprising the steps of:
(a) providing
an electron-optical system for irradiating and scanning a sample having a circuit pattern thereon by a focused electron beam, a detector for detecting back-scattered electrons or secondary electrons from an electron beam-irradiated portion of the sample, an image forming unit for forming an image of the sample based on a detected signal from the detector, and a difference detecting circuit for comparing an image signal obtained by the image forming unit with a reference image signal and thereby detecting a difference between the two image signals;

(b) amplifying an output from the detector using an amplifier having a first amplification factor, the output being obtained by scanning a relatively large region of the sample with the electron beam of a relatively large electric current at a relatively high speed;

(c) then supplying the thus-amplified output to the image forming unit to form an image signal;

(d) comparing the image signal with a similar image signal obtained from another region of the sample, so as to detect a difference between the image signals;

(e) determining coordinates of a position where the difference has occurred;

(f) scanning a region of a smaller area than the relatively large region, including the position of occurrence of the difference, with the electron beam of a smaller electric current than the relatively large electric current and at a lower speed than the relatively high speed;

(g) then supplying the resulting output from the detector to the image forming unit via a circuit provided with an amplifier which amplifies the output at a larger amplification factor than the first amplification factor and is provided with a high-frequency component cut-off filter, to form an image signal; and (h) observing the difference-generating position.

14. A method of inspecting a circuit pattern according to claim 12, wherein in the step (a), the stage is moved continuously in a first direction, and the first electron beam scans the sample in a second direction perpendicular to the first direction; and wherein in the step (b), the stage is held stationary.

* * * * *